United States Patent [19]
Halperin et al.

[11] Patent Number: 5,535,752
[45] Date of Patent: Jul. 16, 1996

[54] IMPLANTABLE CAPACITIVE ABSOLUTE PRESSURE AND TEMPERATURE MONITOR SYSTEM

[75] Inventors: Louis E. Halperin, St. Paul; Brian B. Lee, Golden Valley; Glenn M. Roline, Anoka, all of Minn.; Anthony J. Varrichio, Flanders, N.J.

[73] Assignee: Medtronic, Inc., Minneapolis, Minn.

[21] Appl. No.: 394,860

[22] Filed: Feb. 27, 1995

[51] Int. Cl.$^6$ .................................................. A61N 1/362
[52] U.S. Cl. .......................... 128/670; 128/734; 128/672; 128/673; 128/675
[58] Field of Search ................................. 128/642, 672, 128/670, 673, 675, 734; 607/9, 18, 30

[56] References Cited

U.S. PATENT DOCUMENTS

| | | |
|---|---|---|
| 4,016,764 | 4/1977 | Rice . |
| 4,023,562 | 5/1977 | Hynecek . |
| 4,257,423 | 3/1981 | McDonald . |
| 4,407,296 | 10/1983 | Anderson . |
| 4,432,372 | 2/1984 | Monroe . |
| 4,485,813 | 12/1984 | Anderson . |
| 4,556,063 | 12/1985 | Thompson . |
| 4,750,495 | 6/1988 | Moore . |
| 4,858,615 | 8/1989 | Meinema . |
| 4,967,755 | 11/1990 | Pohndorf . |
| 5,127,404 | 7/1992 | Wyborny . |
| 5,137,019 | 8/1992 | Pedersen et al. ............. 128/734 X |
| 5,324,326 | 6/1994 | Lubin . |

FOREIGN PATENT DOCUMENTS 9413200  6/1994  WIPO .

OTHER PUBLICATIONS

Ko et al. "A Design of Capacitive Pressure Transducer", IEEE Proc. Symp. Boisensors, 1984, p. 32.
Graeger et al. "A ceramic differential-pressure transducer", Phillips Tech. Rev., 43:4:86–93, Feb. 1987.
Jones et al. "The design and some appications of sensitive capacitance micrometers" *Journal of Physics E: Scientific Instruments*, 1973, vol. 6, p. 589.
Dias et al. "Capacitive Blood Pressure Transducer", *ISA Transactions*, vol. 19, No. 3, p. 19.
Chau et al. "An Ultraminiature Solid-State Pressure Sensor for a Cardiovascular Catheter", *Microsensors*, IEEE Press, p. 343, 1991.
Transducers, Chapter 4, Capacitive Transducers, pp. 89 et seq.

*Primary Examiner*—Angela D. Sykes
*Assistant Examiner*—Stephen Huane
*Attorney, Agent, or Firm*—Michael B. Atlass; Harold R. Patton

[57] ABSTRACT

A capacitive pressure and temperature sensing system for providing signals representative of the magnitude of body fluid absolute pressure at a selected site and ambient operating conditions, including body temperature, at the site. An implantable lead having a sensor module formed in its distal end is coupled to a monitor that powers a sensor circuit in the sensor module and demodulates and stores absolute pressure and temperature data derived from signals generated by the sensor circuit. The sensor module is formed with a pickoff capacitor that changes capacitance with pressure changes and a reference capacitor that is relatively insensitive to pressure changes. The sensor circuit provides charge current that changes with temperature variation at the implant site, alternately charges and discharges the two capacitors, and provides timing pulses having distinguishable parameters at the end of each charge cycle that are transmitted to the demodulator. The demodulator detects and synchronizes the timing pulses and derives pressure and temperature analog voltage values representative of the intervals between the timing pulses which are digitized and stored in the monitor. The monitor may also be coupled with other sensors for measuring and storing related patient body parameters, e.g. blood gas, EGM, and patient activity.

18 Claims, 10 Drawing Sheets

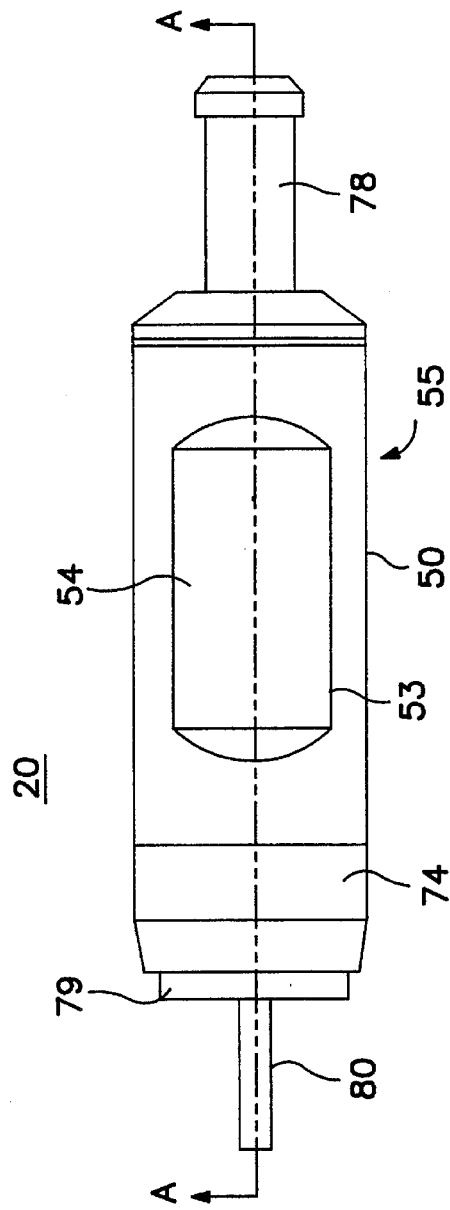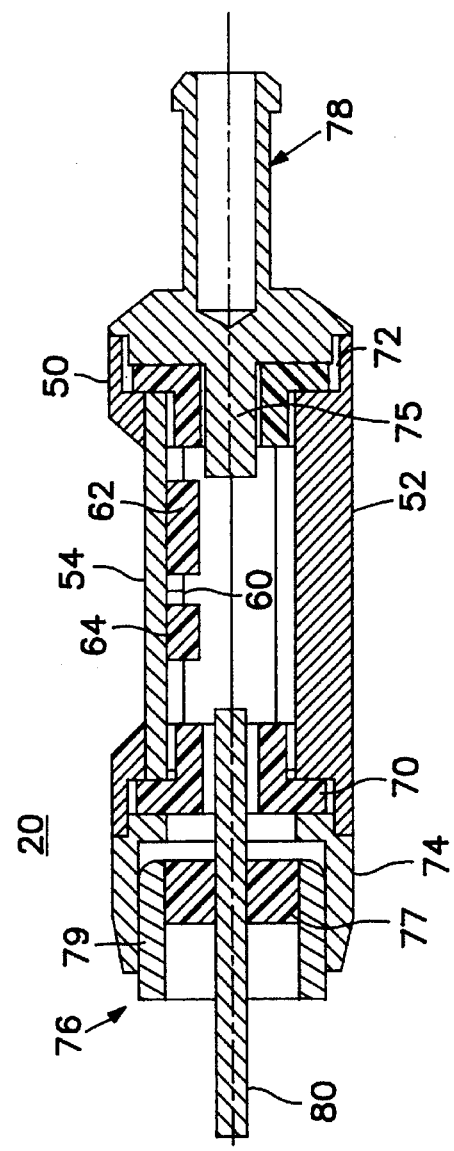
FIG. 4
FIG. 5

IMPLANTABLE CAPACITIVE ABSOLUTE PRESSURE AND TEMPERATURE MONITOR SYSTEM

REFERENCE TO RELATED APPLICATION

Reference is hereby made to commonly assigned, co-pending U.S. patent application Ser. Nos. 08/394,870 and 08/402,681, both pending, filed on even date herewith for IMPLANTABLE CAPACITIVE ABSOLUTE PRESSURE AND TEMPERATURE SENSOR in the names of Keith Meisel et al.

BACKGROUND OF THE INVENTION

1. Field of the Invention

The present invention relates to a body implantable pressure and temperature monitor and data storage system, particularly employing a sensor attached to an endocardial lead for implantation in a right heart chamber, for modulating the sensed intracardiac pressure and temperature, and providing modulated pressure and temperature signals to an implanted or external hemodynamic monitor and/or cardiac pacemaker or pacemaker/cardioverter/defibrillator.

2. Description of the Background Art

Efforts have been underway for many years to develop implantable pressure transducers and sensors for temporary or chronic use in a body organ or vessel and systems for recording absolute pressure. Many different designs and operating systems have been proposed and placed into temporary or chronic use with patients. Indwelling pressure sensors for temporary use of a few days or weeks are available, and many designs of chronically or permanently implantable pressure sensors have been placed in clinical use.

Piezoelectric crystal or piezo-resistive pressure transducers mounted at or near the distal tips of pacing leads, for pacing applications, or catheters for monitoring applications, are described in U.S. Pat. Nos. 4,407,296, 4,432,372, 4,485,813, 4,858,615, 4,967,755, and 5,324,326, and PCT Publication No. WO 94/13200, for example. The desirable characteristics and applications for patient use of such lead or catheter bearing, indwelling pressure sensors are described in these and other patents and the literature in the field. Generally, the piezoelectric or piezoresistive transducers have to be sealed hermetically from blood. Certain of these patents, e.g. the '296 patent, disclose sealing the piezoresistive bridge elements within an oil filled chamber.

U.S. Pat. No. 4,023,562 describes a piezoresistive bridge of four, orthogonally disposed, semiconductor strain gauges formed interiorly on a single crystal silicon diaphragm area of a silicon base. A protective silicon cover is bonded to the base around the periphery of the diaphragm area to form a sealed, evacuated chamber. Deflection of the diaphragm due to ambient pressure changes is detected by the changes in resistance of the strain gauges.

Because the change in resistance is so small, a high current is required to detect the voltage change due to the resistance change. The high current requirements render the piezoresistive bridge unsuitable for long term use with an implanted power source. High gain amplifiers that are subject to drift over time are also required to amplify the resistance-related voltage change.

Other semiconductor sensors employ CMOS IC technology in the fabrication of pressure responsive silicon diaphragm bearing capacitive plates that are spaced from stationary plates. The change in capacitance due to pressure waves acting on the diaphragm is measured, typically through a bridge circuit, as disclosed, for example, in the article "A Design of Capacitive Pressure Transducer" by Ko et al., in *IEEE Proc. Symp. Biosensors,* 1984, p. 32. Again, fabrication for long term implantation and stability is complicated.

In addition, differential capacitive plate, fluid filled pressure transducers employing thin metal or ceramic diaphragms have also been proposed for large scale industrial process control applications as disclosed, for example, in the article "A ceramic differential-pressure transducer" by Graeger et al., *Philips Tech. Rev.,* 43:4:86–93, February 1987. The large scale of such pressure transducers does not lend itself to miniaturization for chronic implantation.

Despite the considerable effort that has been expended in designing such pressure sensors, a need exists for a body implantable, durable, long-lived and low power consuming pressure sensor for accurately sensing absolute pressure waves in the body over many years and for deriving body temperature signals in a system for demodulating and storing the signals.

SUMMARY OF THE INVENTION

It is therefore an object of the present invention to provide a monitor system for accurately detecting absolute blood pressure signals and related signals and converting the signals to digitized data.

In accordance with the invention, a capacitive pressure and temperature sensing system for providing signals representative of the magnitude of body fluid absolute pressure at a selected site and ambient operating conditions, including body temperature, at the site comprises: an elongated implantable lead body having proximal and distal end sections and having first and second electrical conductors extending from the proximal end section to the distal end section, the distal end section adapted to be implanted in a selected body site; a sensor module formed in the distal end section of the lead body having pickoff and reference capacitor means formed therein; sensor circuit means within the sensor module electrically connected to the pickoff and reference capacitor means and the first and second electrical conductors including temperature conversion means for generating a charge current and a discharge current varying with ambient temperature at the selected site, charging and discharging means for alternately charging and discharging the pickoff and reference capacitor means with the charge and discharge currents between selected voltage levels, and pulse generating means for generating pickoff and reference timing pulses separating pressure related and temperature related charge time intervals of the pickoff and reference capacitor means varying as a function of the charge current and capacitance changes of the pickoff capacitor means; means for providing a bias voltage and current to the first and second electrical conductors for powering the sensor circuit means; and demodulating means coupled to the first and second conductor means and responsive to the pickoff and reference timing pulses for discriminating and converting the pressure and temperature related time intervals into pressure and temperature signals.

Preferably the demodulating means further comprises: discriminating means for discriminating the pressure and temperature related charge time intervals from the pressure and reference timing pulses; temperature signal processing channel means for converting the temperature related charge time intervals into a temperature signal having a magnitude dependent on the temperature induced changes in the charge current affecting the charge time of the reference capacitor means; and pressure signal processing channel means for converting the duty cycle of the successive pressure and related charge time intervals into a pressure signal having a magnitude dependent on the pressure induced changes in capacitance of the pickoff capacitor means and also dependent on temperature induced changes in the charge current affecting the charge time of the pickoff capacitor means and the reference capacitor means.

The monitor system preferably further comprises means for converting the pressure and temperature signals into digitized data, and means for storing the digitized data for retrieval.

The sensor lead is preferably constructed such that the first plate of the pickoff capacitor means is formed of a pressure deformable, planar diaphragm having a first predetermined surface area formed by the module housing of a conductive material with an exterior planar surface and a parallel interior surface within the hermetically sealed chamber, the planar diaphragm adapted to be deformed in the first predetermined surface area by variations in fluid pressure outside the module housing; and the first plate of the reference capacitor means is formed by a second predetermined planar surface area of the interior surface spaced apart from and co-planar with the first predetermined surface area and substantially non-deformable by variations in fluid pressure outside the module housing.

BRIEF DESCRIPTION OF THE DRAWING

These and other objects, advantages and features of the present invention will be more readily understood from the following detailed description of the preferred embodiments thereof, when considered in conjunction with the drawings, in which like reference numerals indicate identical structures throughout the several views, and wherein:

FIG. 4 is a top subassembly drawing of the pressure sensing module incorporated into the distal end of the pressure sensing lead of FIG. 2;

FIG. 5 is a side cross-section view of the internal components of the pressure sensing module taken along line A—A of FIG. 4;

DETAILED DESCRIPTION OF THE PREFERRED EMBODIMENTS

The capacitive pressure sensing lead 12 of the present invention is designed to chronically transduce blood pressure from the right ventricle of the heart over the range of absolute pressures from 400–900 mm Hg, and within the frequency range of 0–100 Hz. The lead 12 is primarily employed with an implantable, battery powered monitor 100 which employs a microprocessor based demodulation, data storage and telemetry system for sampling and storing blood pressure data at programmed intervals and telemetering out the accumulated data to an external programmer/transceiver on receipt of a programmed-in command, in the manner of current, conventional multi-programmable pacemaker technology. The lead 12 is intended to be implanted transvenously into the right heart chambers in the same manner as a conventional pacing lead, except that the distal end, including the pressure sensor module, may be advanced out of the right ventricle into the pulmonary artery to monitor blood pressure in that location. The monitor is intended to be implanted subcutaneously in the same manner that pacemakers are implanted.

Monitor and Lead System Overview

Figure 1:
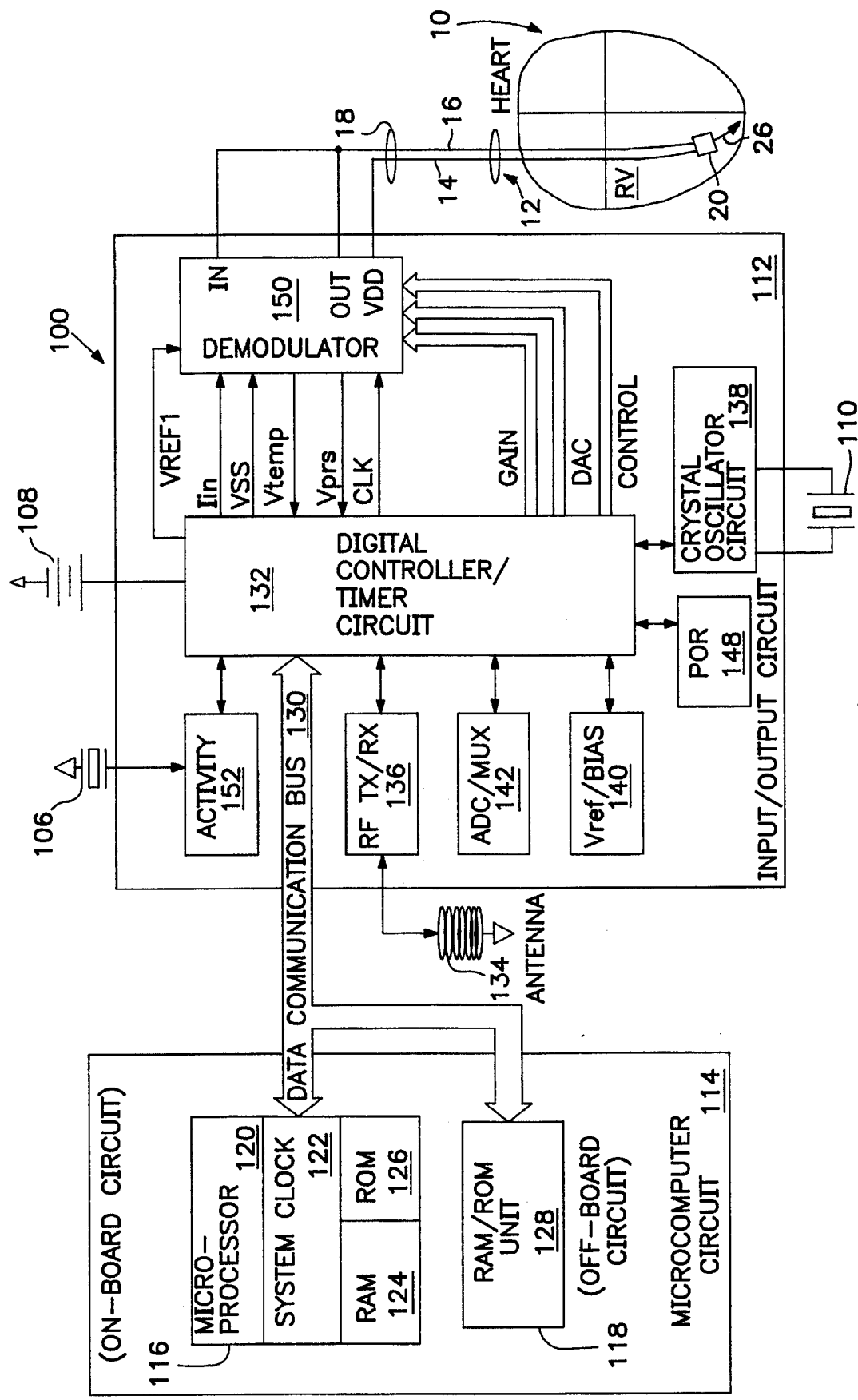
FIG. 1 is block level diagram of an implantable, programmable blood pressure monitor and lead system of the present invention.

FIG. 1 is a simplified block diagram of the patient's heart 10 in relation to the pressure sensing lead 12 and monitor 100. The lead 12 has first and second lead conductors 14 and 16 extending from a proximal connector end 18 to the pressure sensor module 20 disposed near the distal tine assembly 26. The pressure sensor module 20 includes a variable pickoff capacitor and a fixed reference capacitor and signal modulating circuit described below in reference to FIGS. 4–12 which develops both blood pressure and temperature time-modulated intervals. The proximal connector assembly is formed as a conventional bipolar, in-line pacing lead connector and is coupled to the monitor connector (not shown) which is formed as a conventional bipolar in-line pacemaker pulse generator connector block assembly. The tine assembly 26 comprises soft pliant tines adapted to catch in heart tissue to stabilize the lead in a manner well known in the pacing art. The detailed construction of the lead 12 is described below in conjunction with FIGS. 2 and 3.

The monitor 100 is divided generally into an input/output circuit 112 coupled to a battery 108, an optional activity sensor 106, a telemetry antenna 134, the lead conductors 14, 16, a crystal 110, and a microcomputer circuit 114. The input/output circuit 112 includes the digital controller/timer circuit 132 and the associated components including the crystal oscillator 138, power-on-reset (POR) circuit 148, Vref/BIAS circuit 140, ADC/MUX circuit 142, RF transmitter/receiver circuit 136, optional activity circuit 152 and pressure signal demodulator 150.

Crystal oscillator circuit 138 and crystal 110 provide the basic timing clock for the digital controller/timer circuit 132. Vref/BIAS circuit 140 generates stable voltage reference Vref and current levels from battery 108 for the circuits within the digital controller/timer circuit 132, and the other identified circuits including microcomputer circuit 114 and demodulator 150. Power-on-reset circuit 148 responds to initial connection of the circuitry to the battery 108 for defining an initial operating condition and also resets the operating condition in response to detection of a low battery voltage condition. Analog-to-digital converter (ADC) and multiplexor circuit 142 digitizes analog signals Vprs and Vtemp received by digital controller/timer circuit 132 from demodulator 150 for storage by microcomputer circuit 114.

Data signals transmitted out through RF transmitter/receiver circuit 136 during telemetry are multiplexed by ADC/MUX circuit 142. Voltage reference and bias circuit 140, ADC/MUX circuit 142, POR circuit 148, crystal oscillator circuit 138 and optional activity circuit 152 may correspond to any of those presently used in current marketed, implantable cardiac pacemakers.

The digital controller/timer circuit 132 includes a set of timers and associated logic circuits connected with the microcomputer circuit 114 through the data communications bus 130. Microcomputer circuit 114 contains an on-board chip including microprocessor 120, associated system clock 122, and on-board RAM and ROM chips 124 and 126, respectively. In addition, microcomputer circuit 114 includes an off-board circuit 118 including separate RAM/ROM chip 128 to provide additional memory capacity. Microprocessor 120 is interrupt driven, operating in a reduced power consumption mode normally, and awakened in response to defined interrupt events, which may include the periodic timing out of data sampling intervals for storage of monitored data, the transfer of triggering and data signals on the bus 130 and the receipt of programming signals. A real time clock and calendar function may also be included to correlate stored data to time and date.

In a further variation, provision may be made for the patient to initiate storage of the monitored data through an external programmer or a reed switch closure when an unusual event or symptom is experienced. The monitored data may be related to an event marker on later telemetry out and examination by the physician.

Microcomputer circuit 114 controls the operating functions of digital controller/timer 132, specifying which timing intervals are employed, and controlling the duration of the various timing intervals, via the bus 130. The specific current operating modes and interval values are programmable. The programmed-in parameter values and operating modes are received through the antenna 134, demodulated in the RF transmitter/receiver circuit 136 and stored in RAM 124.

Data transmission to and from the external programmer (not shown) is accomplished by means of the telemetry antenna 134 and the associated RF transmitter and receiver 136, which serves both to demodulate received downlink telemetry and to transmit uplink telemetry. For example, circuitry for demodulating and decoding downlink telemetry may correspond to that disclosed in U.S. Pat. No. 4,556,063 issued to Thompson et al. and U.S. Pat. No. 4,257,423 issued to McDonald et al., while uplink telemetry functions may be provided according to U.S. Pat. No. 5,127,404 issued to Wyborny et al. Uplink telemetry capabilities will typically include the ability to transmit stored digital information as well as real time blood pressure signals.

A number of power, timing and control signals described in greater detail below are applied by the digital controller/timer circuit 132 to the demodulator 150 to initiate and power the operation of the pressure sensor module 20 and selectively read out the pressure and temperature signals Vprs and Vtemp. An active lead conductor 16 is attached through the connector block terminals to input and output terminals of demodulator 150 which supplies a voltage VREG at the output terminal. A passive lead conductor 14 is coupled through to the VDD supply terminal of the demodulator 150. The voltage signals Vprs and Vtemp developed from intervals between current pulses received at the input terminal are provided by demodulator 150 to the digital controller/timer circuit 132. The voltage signals Vprs and Vtemp are converted to binary data in an ADC/MUX circuit 142 and stored in RAM/ROM unit 128 in a manner well known in the art.

As depicted in FIG. 1, the monitor 100 periodically stores digitized data related to blood pressure and temperature at a nominal sampling frequency which may be related to patient activity level, both optionally correlated to time and date and patient initiated event markers. The monitor 100 may also optionally include a further lead connector for connection with further lead for implantation in the right heart having an exposed unipolar distal electrode from which an electrogram (EGM) may be derived. The further lead may also have an oxygen sensor module in the distal segment of the lead. Such a lead is shown in commonly assigned U.S. Pat. No. 4,750,495 to Moore and Brumwell, incorporated herein by reference. That modification of the monitor 100 would also include an EGM sense amplifier (using the monitor case as an indifferent electrode) and an oxygen sensor demodulator and is also described in the above-incorporated '495 patent.

In that optional configuration, the EGM signal may be employed to identify the onset of a cardiac depolarization in each heart cycle and initiate either the monitoring and storage operations or simply initiate the storage of the data derived by continuous monitoring which would otherwise not be stored. In accordance with the preferred embodiment of the invention, the monitored parameters including patient activity, blood pressure and temperature, blood oxygen or other gas saturation level and EGM are all continuously monitored.

The blood pressure signals are preferably digitized and stored at a sample period of every 4.0 ms or 256 Hz sampling frequency. As shown below, this frequency is about one-tenth of the operating frequency of the sensor module 20. The blood temperature signals are preferably digitized and stored once during every sensed EGM heart depolarization cycle. The digitized data values are stored on a FIFO basis between periodic telemetry out of the stored data for permanent external storage. Then, the data may be analyzed externally to identify the portions of the cardiac cycle of interest and to perform other diagnostic analyses of the accumulated data. Preferably, the external programmer can also program the monitor 100 to telemeter out the digitized data values in real time at the same or different sampling frequencies. The sampled and stored blood pressure data are absolute pressure values and do not account for changes in barometric pressure affecting the ambient pressure load on the pressure sensor module 20. Physicians typically measure blood pressure in relation to atmospheric pressure. Thus, it may be necessary to separately record atmospheric pressure data with separate measuring and recording equipment. At present, a separate, portable pressure recording unit (not shown) worn externally by the patient to record atmospheric pressure is contemplated to be used with the system of the present invention. The atmospheric pressure and a time and date tag are preferably recorded in the external unit at periodic, e.g. one minute, intervals. The atmospheric pressure data is intended to be read out from the external unit when the absolute pressure and optional other data stored in RAM/ROM unit 128 is telemetered out and the data correlated by time and date and employed by the physician to derive diagnoses of the patient's condition.

Pressure Sensor/Lead Construction

The pressure sensor capsule or module 20 is constructed with a titanium outer housing having an integral, pressure deformable, planar sensing membrane or diaphragm formed in it as one plate of a variable or pickoff capacitor $C_P$. The other plate of the pickoff capacitor $C_P$ is fixed to one side of a hybrid circuit substrate hermetically sealed within the outer housing. The capacitance of pickoff capacitor $C_P$ varies as the diaphragm is deformed by pressure waves associated with heart beats in the patient's heart 10 or elsewhere in the vascular system. A reference capacitor $C_R$ is also formed with fixed spacing between planar capacitor plates formed on the same side of the hybrid circuit substrate and on the outer housing to provide a reference capacitance value. The pressure (and temperature) sensor circuitry within the module 20 employs the voltages VDD and VREG supplied by the demodulator 150 to alternately charge and discharge the capacitor pair with charge and discharge currents that vary with temperature and to provide instantaneous absolute pressure and temperature modulated charge time intervals to the demodulator 150 in a manner described below.

Figure 2:
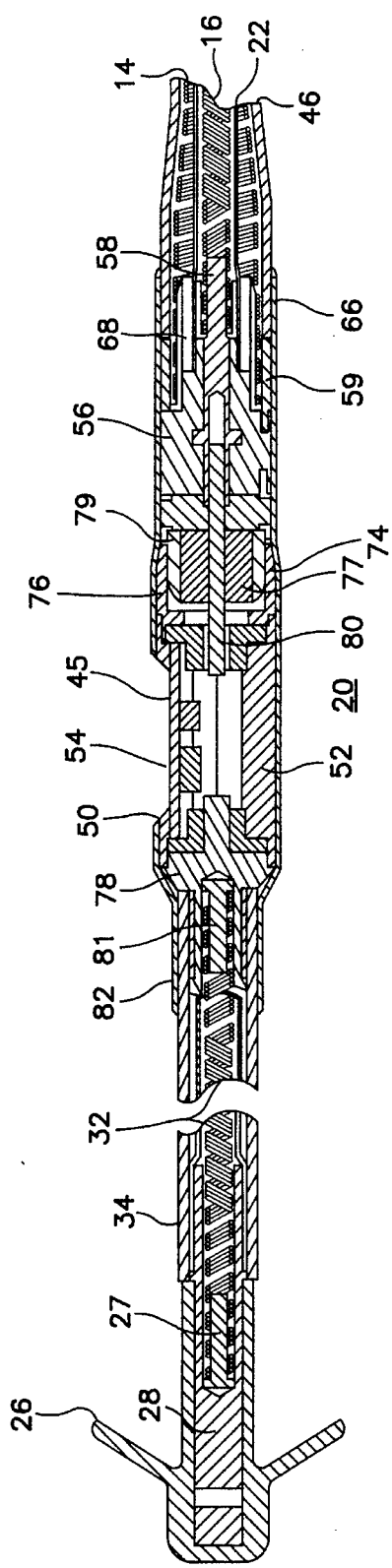
FIG. 2 is a cross-section assembly view of the distal end of a pressure sensing lead employed in the system of FIG. 1.
Figure 3:
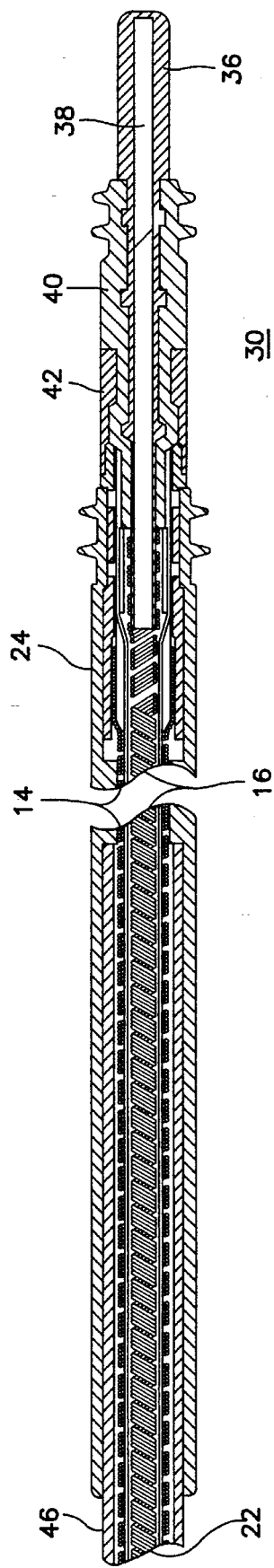
FIG. 3 is a cross-section assembly view of the proximal end of a pressure sensing lead employed in the system of FIG. 1.

FIGS. 2 and 3 are cross-section views of the distal and proximal end sections of the lead 12 of FIG. 1. The pressure sensor module 20 is located just proximal to the distal tip tine assembly 26 and is mechanically and electrically connected to the coaxial, outer and inner, coiled wire lead conductors 14 and 16. The passive and active, coiled wire lead conductors 14 and 16 are separated by an inner insulating sleeve 22 and encased by an outer insulating sleeve 46 extending between in-line connector assembly 30 and the pressure sensor module 20. A stylet receiving lumen is formed within the inner coiled wire lead conductor 16 and extends to the connection with the sensor module 20.

The in-line connector assembly 30 includes an inner connector pin 36 having a styler receiving, pin lumen 38 and is attached to the proximal end of the inner coiled wire conductor 16 to align the pin lumen 38 with the stylet receiving lumen of the inner coiled wire conductor 16. An insulating sleeve 40 extends distally over the inner connector pin 36 and separates it from a connector ring 42. Connector ring 42 is electrically and mechanically attached to the proximal end of the outer coiled wire conductor 14. An exterior insulating connector sleeve 24 extends distally from the connector ring 42 and over the proximal end of the outer sleeve 46.

The distal ends of the outer and inner coiled wire conductors 14 and 16 are attached to the proximal end of the pressure sensor module 20 to provide the VDD and the input/output connections to the on-board pressure sensor hybrid circuit described below. A further coiled wire segment 32 extends between the tine assembly 26 and the distal end of the pressure sensor module 20 and is covered by a further insulating sleeve 34. The tine assembly 26 surrounds and electrically insulates inner metal core 28 that is mechanically attached to the distal end of the coiled wire segment 32.

The materials used for these components of the pressure sensing lead 12 and the construction and attachments depicted in FIGS. 2 and 3 are conventional in the art of bipolar, coaxial pacing lead technology having an in-line connector. Such lead technology is incorporated in the fabrication of the Medtronic® bipolar pacing lead Model 4004M. The specific materials, design and construction details are not important to the understanding and practice of the present invention. In this particular illustrated embodiment, the pressure sensing lead 12 is not also employed as a pacing lead, but the pressure sensing module 20 could be incorporated into a pacing lead, particularly for use in control of rate responsive pacemakers and pacemaker-cardioverter-defibrillators.

Figure 6:
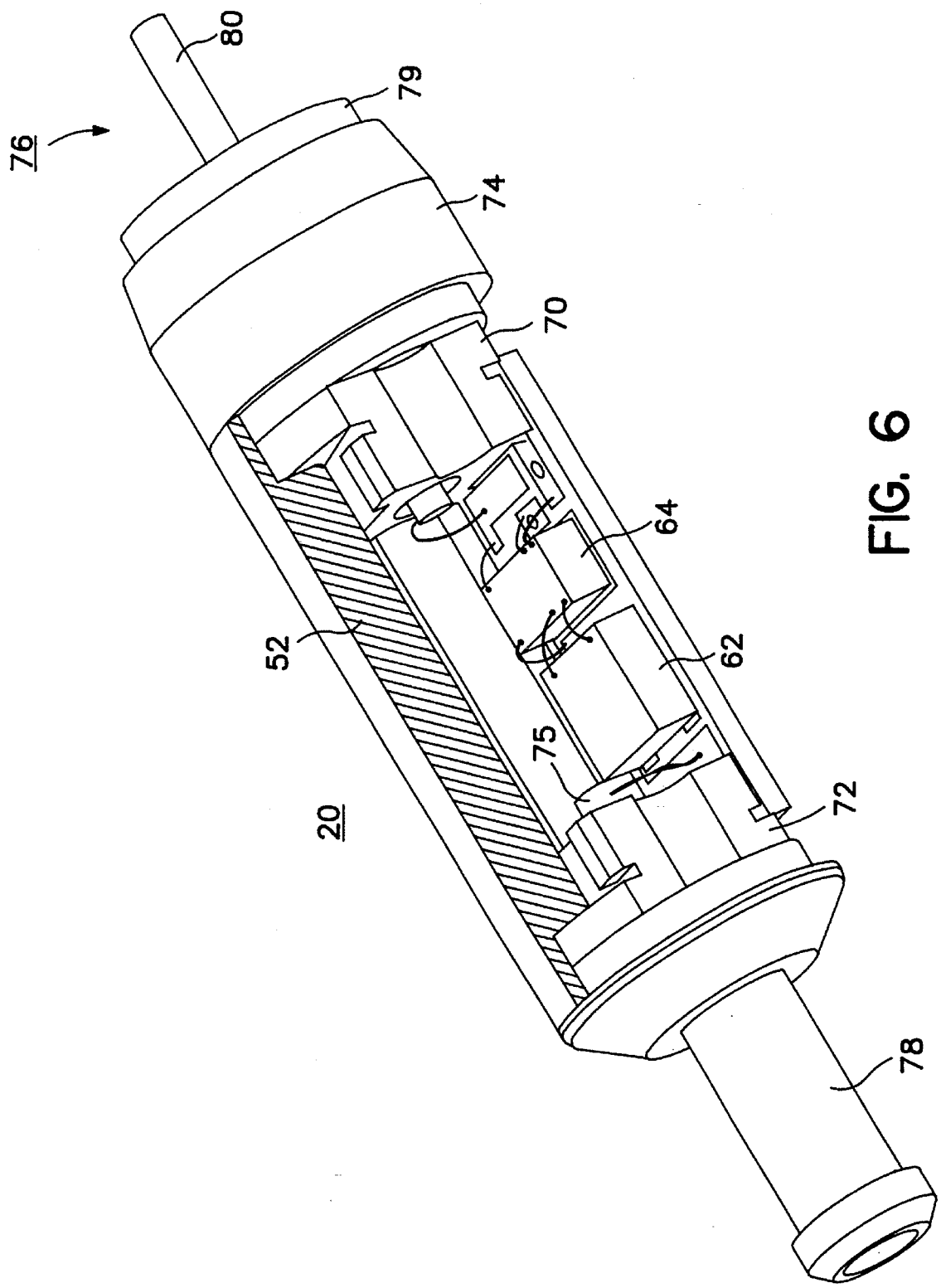
FIG. 6 is a partial cutaway perspective view of the attachment of the pressure and temperature signal modulating circuit to the feedthrough and housing of the pressure sensing module.
Figure 7:
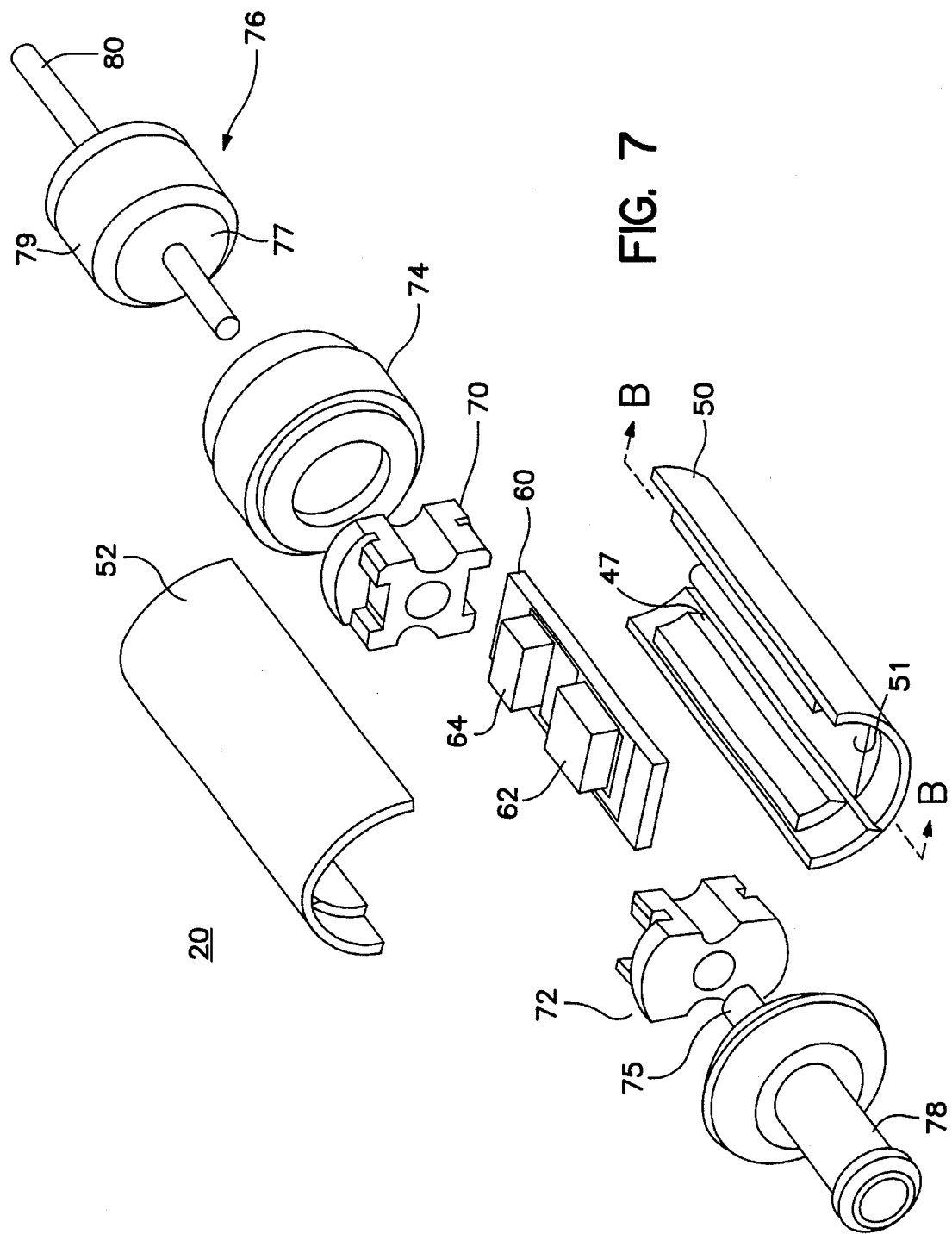
FIG. 7 is an exploded perspective view of the components of the pressure sensing module.

Turning to the construction of the pressure sensing capsule or module 20, reference is first made to the assembly drawings, including the enlarged top and side cross-section views of FIGS. 4 and 5, the partial section view of FIG. 6 and the exploded view of FIG. 7. The pressure sensing module 20 is formed with a first and second titanium outer housing half members 50 and 52 which when joined together as assembled titanium housing 55 surround a ceramic hybrid circuit substrate 60 supporting the sensing and reference capacitors and pressure signal modulating circuit. The pressure signal modulating circuit (described in detail below with reference to FIGS. 10 and 11) includes a resistor 62 and IC chip 64 mounted to one surface of the substrate 60 and attached to electrical terminal pads and board feedthroughs to the other surface thereof. The substrate 60 is supported in a manner described below in a fixed relation with respect to housing member 52 by the proximal and distal silicone rubber cushions 70 and 72 and the parallel side walls 47 and 49 (shown in FIGS. 7 and 8). The proximal silicone rubber cushion 70 also bears against the titanium adaptor ring 74 that receives the feedthrough 76. The feedthrough 76 includes a ceramic insulator 77 between the feedthrough ferrule 79 and feedthrough wire 80 to electrically isolate feedthrough wire 80 that is electrically connected to a pad of the substrate 60. The distal silicone rubber cushion 72 bears against the nose element 78 which is electrically connected to a further pad of the substrate 60.

Internal electrical connections between the sensor IC chip 64 and the substrate are made via aluminum wire-bonds as shown in FIG. 6. Connections between the hybrid traces and both the feedthrough pin 80 and the nose element extension pin 75 are also made via gold wire-bonds. Conventional wire-bonding is used with each trace, while the connections to the pins 75 and 80 are made using conductive silver epoxy. The specific electrical connections are described below in conjunction with the electrical schematic diagram of the sensor module electronic circuit in FIG. 11.

After the mechanical and electrical components of the pressure sensing module 20 are assembled together, the titanium housing half members 50 and 52 and the nose element and adaptor ring 74 are laser welded together as hermetically sealed, assembled titanium housing 55. Then, the module 20 is attached to the components of the lead 12 to provide the electrical and mechanical connections with the outer and inner, passive and active, coiled wire lead conductors 14 and 16 as described below.

As shown in FIG. 2, the module 20 is electrically and mechanically attached to the outer and inner coiled wire conductors 14 and 16 at the proximal end thereof through an intermediate transition assembly similar to a feedthrough and including an insulating body 56 separating an inner, conductive transition pin 58 from distal and proximal outer conductive transition sleeves 57 and 59. Sleeves 57 and 59 are laser welded together for electrical and mechanical connection.

The distal transition sleeve 57 is welded to the ferrule 79 and the distal end of the transition pin 58 is staked to the feedthrough pin 80. The distal end of the inner transition pin 58 is hollow and extends out of the insulating body 56 to receive the proximal end of the feedthrough pin 80. Staking is accomplished through access ports in the molded insulating body 56, and then the access ports are filled with silicone adhesive. In this fashion, the inner transition pin 58 is electrically coupled to the feedthrough pin 80, and the outer transition sleeves 57 and 59 are electrically connected to the assembled titanium housing 55.

The proximal end of the inner transition pin 58 is slipped into the distal lumen of the inner coiled wire conductor 16. The distal end of the inner coiled wire conductor 16 is crimped to the proximal end of the inner transition pin 58 by force applied to a crimp sleeve 66 slipped over the distal segment of the coiled wire conductor 16. The distal end of inner insulating sleeve 22 is extended over the crimp sleeve 66 and adhered to the insulating body 56 to insulate the entire inner conductive pathway. The outer coiled wire conductor 14 is attached electrically and mechanically by crimping it between the outer transition sleeve 59 and an inner crimp core sleeve 68 slipped between the distal lumen of the outer coiled wire conductor 14 and the inner insulating sleeve 22. Silicone adhesive may also be used during this assembly. When the electrical and mechanical connections are made, the active coiled wire conductor 16 is electrically connected to a pad or trace of the substrate 60, and the passive coiled wire conductor 14 is electrically attached through the housing half members 50 and 52 to a further substrate pad or trace as described below.

The distal end of the pressure sensing module 20 is attached to the distal lead assembly including further outer sleeve 34 and coiled wire conductor 32 described above. At the distal end of the pressure sensing module 20, a crimp pin 81 is inserted into the lumen of the further coiled wire conductor. The crimp pin 81 and the further coiled wire conductor 32 are inserted into the tubular nose element 78 which is then crimped to the coiled wire conductor 32 and crimp pin 81. The further outer sleeve 34 extends over the crimp region and the length of the further coiled wire conductor 32. The distal end of the further coiled wire conductor 32 is attached by a similar crimp to the inner tip core member 28 using a further crimp pin 27.

Figure 8:
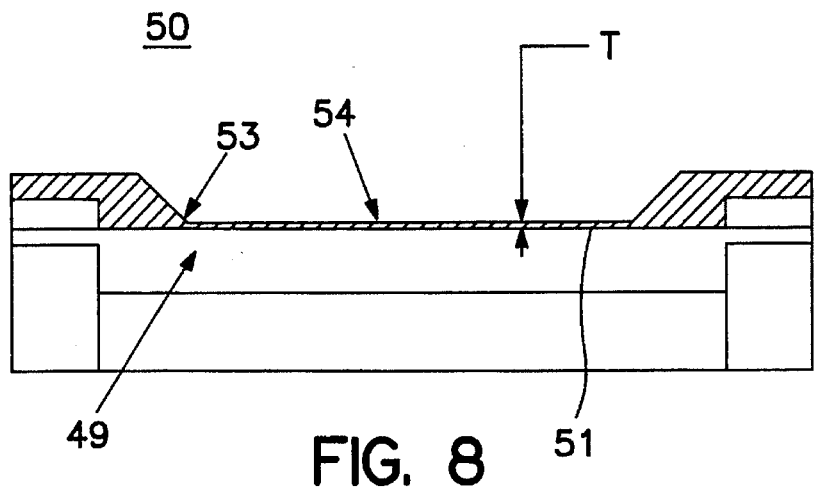
FIG. 8 is a side cross section view of a housing member and diaphragm taken along line B—B of FIG. 7.
Figure 9:
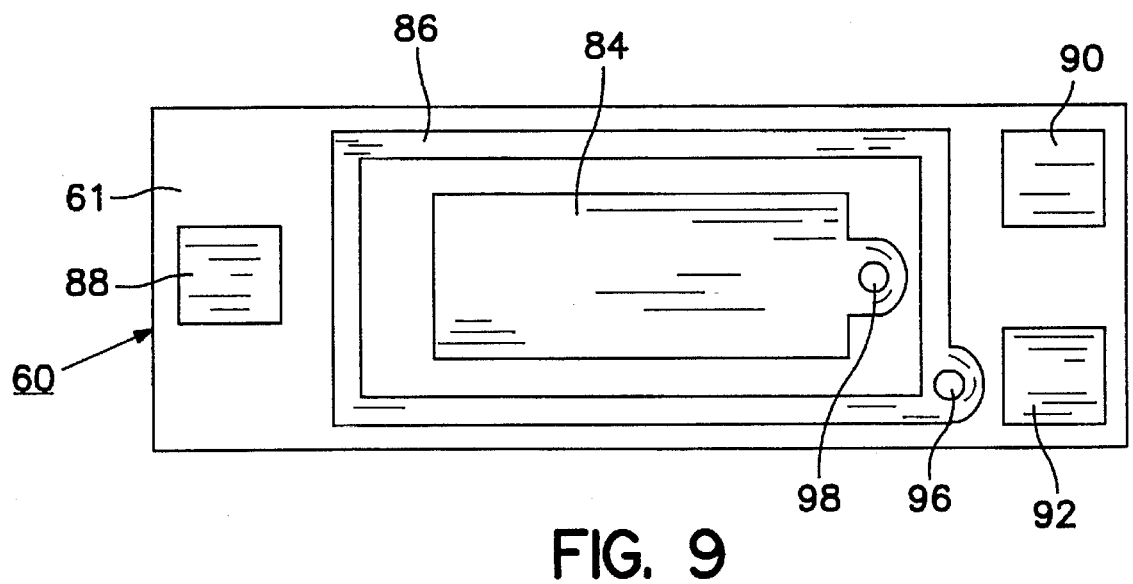
FIG. 9 is a bottom view of the IC hybrid circuit substrate of FIG. 7.

Returning to FIGS. 4 and 5, and in reference to FIG. 8, thin titanium diaphragm 54 is machined into the titanium outer housing half member 50. The flat inner surface of diaphragm 54 and a peripheral continuation of that surface form plates of a pair of planar capacitors, the other plates of which are deposited onto the adjacent surface 61 of the ceramic hybrid substrate 60 as shown in FIG. 9. An external pressure change results in displacement of the diaphragm 54 and subsequent change in capacitance between the diaphragm 54 and one of the deposited substrate plates. This change in capacitance of the pickoff capacitor $C_P$ with change in pressure is approximately linear over the pressure range of interest, and is used as a measure of the pressure outside the sensor module 20. The external pressure change has little effect on the second, reference capacitor $C_R$.

To electrically isolate diaphragm 54 from the patient's body, materials must be used that do not significantly absorb body fluids and swell, which in turn causes diaphragm 54 deflection and changes the capacitance of the pickoff capacitor $C_P$. The material must be uniformly thin and repeatable during manufacture so as to avoid affecting sensitivity of the pickoff capacitor $C_P$. Also, the material must adhere very well to the diaphragm 54 so that bubbles, gaps or other separations do not occur over time. Such separations could cause hysteresis or lag of the sensed capacitance change.

Returning to FIG. 2, the outer sleeve 46 and further sleeve 34 are formed of conventional urethane tubes employed in fabricating pacing leads. For adherence to outer sleeve 46 and further sleeve 34, a thin urethane sensor jacket or covering 82 is employed that extends over the full length of the sensor module 20 and is adhered at its ends to the outer insulating sleeve 46 and the further outer insulating sleeve 34, e.g. as by urethane based adhesives. The urethane covering 82 is employed to cover the majority of the sensor module 20 but the material does not always adhere well to the metal surfaces thereof, even when a primer is employed. The loss of adherence over the diaphragm 54 can lead to accumulation of fluids and affect the response time to changes in blood pressure. Therefore, it is necessary to substitute a better adhering, body compatible, insulating coating over the diaphragm 54.

In order to do so, a cut-out portion of the sensor covering 82 is made following the periphery 53 in order to expose the diaphragm or diaphragm 54. A thin, uniform thickness coating 45 of silicone adhesive is applied over the exposed diaphragm 54 that adheres thereto without any fluid swelling or separation occurring over time. The silicone adhesive does not adhere well to the edges of the cut-out section of the urethane covering 82, but can be injected between the edges and the half member 50 to fill up any remaining edge gap.

The resulting composite covering 82 and insulating layer electrically insulates the titanium outer housing half members 50 and 52 that are electrically connected to VDD. The combined housing is formed by welding the half members 50 and 52 together and to the adaptor ring 74 and nose element 78. When assembled, the sensor capsule or module 20 is preferably about 0.140 inches in diameter, including the polyurethane insulation covering 82, and is approximately 0.49 inches long.

The cylindrical housing half members 50 and 52 are machined in the two pieces using wire electric discharge machining (EDM) methods. In the first housing half member 50, the thin diaphragm 54 is approximately 0.0013 inches thick at T in FIG. 8 and is produced through precision EDM of the interior and exterior surfaces of the titanium stock. The inner surface 51 of the half member 50 extends as a continuous planar surface beyond the perimeter 53 of the diaphragm 54 to provide one plate of the reference capacitor $C_R$ in that region.

Turning to FIG. 9, the ceramic sensor hybrid circuit substrate 60 consists of a 90% alumina board, on the back side 61 of which are deposited an inner, rectangular capacitor plate 84 coupled to a plated substrate feedthrough 98, an outer, ring shaped capacitor plate 86 coupled to a plated substrate feedthrough 96, and three plated standoffs 88, 90, 92. The inner capacitor plate 84 is dimensioned to generally conform to the shape of the diaphragm 54 and fall within the perimeter 53. The perimeter or ring-shaped capacitor plate 86 is dimensioned to fall outside or just inside or to straddle the perimeter 53. The inner surface 51 of half member 50 provides a reference surface for locating the capacitor plates 84 and 86 relative to the diaphragm 54.

When assembled, the plates 84 and 86 are spaced from the inner surface 51 of the housing half member 50 by the difference in thicknesses of the standoffs 88–92 and the plates 84 and 86 to form the pickoff capacitor $C_P$ and reference capacitor $C_R$. The pressure sensing pickoff capacitor $C_P$ employing central capacitor plate 84 varies in capacitance with pressure induced displacement of the diaphragm 54 and the silicone adhesive layer applied thereto. The reference capacitor $C_R$, employing the perimeter reference capacitor plate 86 located in the region where diaphragm 54 deflection is negligible within the operating pressure range, varies in capacitance with common mode changes in sensor voltages, thermal expansion effects, and changes in the hermetically sealed capacitor dielectric constant.

The two capacitor plates 84 and 86 are electrically connected to the front side of the substrate 60, on which the sensor electronic circuit included in the IC chip 64 and the resistor 62 are mounted. The common capacitor plate surface 51 is coupled to VDD. The sensor electronic circuit alternately charges and discharges the pickoff and reference capacitors $C_P$ and $C_R$ through a constant current source which varies with temperature change inside the sensor module 20. The temperature-related changes in the charging current affects the charge times for both the pickoff and reference capacitors $C_P$ and $C_R$ equally. However, temperature induced changes in internal pressure within the sensor module 20 (and external pressure changes) only affect the pickoff capacitor $C_P$ plate spacing, which causes an increase or decrease in the capacitance and subsequent increase or decrease in the time to charge the pickoff capacitor $C_P$ to a set voltage level.

Blood pressure changes cause an increase or decrease of the pickoff capacitor $C_P$ plate spacing, which causes a decrease or increase, respectively, in the capacitance and subsequent decrease or increase, respectively, in the time to charge the pickoff capacitor $C_P$ to a set voltage level, assuming an unchanged blood temperature and constant charging current. Since no significant gap change between common plate surface 51 and the perimeter capacitor plate 86 due to pressure change occurs at the reference capacitor $C_R$, there is little pressure induced reference capacitance change. The ratio of the charging time of the pickoff capacitor $C_P$ to the sum charging time of the reference and pickoff capacitors $C_R$ and $C_P$ provides a stable indication of pressure induced changes and cancels out common mode capacitance changes, resulting in an absolute pressure signal. The common mode capacitance change, principally temperature related, can be derived from the capacitance of the reference capacitor $C_R$. The signals Vprs and Vtemp can also be time correlated to EGM, activity signals and blood gas signals and all stored in memory for later telemetry out.

The substrate surface 61 platings shown in FIG. 9 are specially designed to provide precise control of the pickoff and reference capacitor gaps without the need for an excessive number of close-tolerance components. By specifying a single tight tolerance between the top surfaces of the standoff platings and the top surfaces of the capacitor platings, the spacing between the reference and pickoff capacitor plates and the planar surface 51 of the sensor diaphragm 54 can be very accurately controlled. Because the inner surface 51 of the diaphragm 54 extends beyond the perimeter 53 of the diaphragm 54 to the region where the standoffs 88–92 make contact, the difference between the height of the standoff pads and the height of the capacitor plates 84 and 86 will define the gap between the capacitor plates 84, 86 and the inner surface 51.

The hybrid standoffs 88–92 are pressed into contact against the inner surface 51 by the compressible molded silicone rubber cushions 70, 72 when the components are assembled. The assembly creates an interference fit exerting pressure between the surface 51 and the standoffs 88–92. Lateral constraint of the substrate 60 is provided by the fit of the hybrid circuit substrate 60 in the housing half member 50 between the lateral side walls 47 and 49 in one axis, and by the silicone rubber cushions 70, 72 along the other axis. In a variation, the rubber cushions 70, 72 may be eliminated in favor of simply adhering the side edges of the substrate 60 to the side walls 47 and 49 and/or the end edges to the inner surface 51 of the half member 50. Or the adhesive could be used with the rubber cushions 70, 72. Furthermore, in each assembly variation, the standoffs 88–92 could be bonded to the inner surface 51. The result is an accurate and permanent location of the substrate 60 within the cavity of the sensor module 20 with no residual stress in the critical parts which might cause drift of the sensor signal over time.

This approach to spacing the pickoff and reference capacitor $C_P$ and $C_R$ plates has two major advantages. First, only one set of features, that is the plating heights or thicknesses, need to be in close tolerance, and those features are produced through a process which is extremely accurate. For, example, the standoffs 88, 90, 92 can be precisely plated to a thickness of 0.0011, and the capacitor plates 84, 86 can be plated to 0.005 inches. A gap of 0.0006 inches with a tolerance of 0.0001 inches can thereby be attained between the capacitor plates 84, 86 and the diaphragm inner surface 51. The second advantage is the near absence of signal modulation by thermal expansion effects. Thermal change in dimension of the structure which establishes the gap between the plates 84, 86 and the sensor diaphragm inner surface 51 is per the relation $\Delta l = \alpha \Delta T \, l$, where $\Delta l$ is the change in gap, $\alpha$ is the thermal expansion coefficient of the material creating the gap, $\Delta T$ is the variation in temperature, and $l$ the length of the structure.

In the example provided, the gaps are only 0.0006" thick, so change in gap over an expected variation in temperature in vivo of 1° C., assuming coefficient of thermal expansion for the standoff material of around $13 \times 10^{-6}$/°C., would result in a gap change of 7.8 nano-inches. This thermal change is about sixty times less than the gap change for 1 mm Hg pressure change, and much less than be detected using state of the art low-current methods.

There is one significant thermal effect. When the pressure sensor module 20 is sealed using a laser weld process, a volume of gas (mostly Argon and Nitrogen) at or near atmospheric temperature and pressure is trapped inside the cavity of the sensor module 20. The difference between the gas pressure inside the cavity and the outside pressure influences the gap of the pickoff capacitor $C_P$. At the instant the sensor is sealed, there is zero pressure differential and consequently no deflection of the pressure diaphragm 54 from its neutral position. But the gas inside the sensor must comply with the classical gas law PV=nRT. Assuming then that the volume inside the sensor is constant, and that the mass quantity and gas constant (n and R, respectively) are constant (since no gas enters or leaves the sensor cavity after sealing), the effect of temperature change can be described by the gas law formula as $P_2 = P_1 (T_2/T_1)$.

In the human body, and particularly the venous blood stream in the ventricle, the temperature may vary from the nominal 37° C. (±2° C.). The variation may be between ±3° C. with fever and between −1° C. to +2° C. with exercise. Assuming that the sensor were sealed at 300K and 760 mm Hg, the gas law formula implies that for every 1° C. change in temperature there is a corresponding change of over 2 mm Hg in internal pressure. This will manifest itself as a decrease in the pressure value reported by the sensor with increasing temperature, since the cavity pressure against which external pressure is compared has increased. This is a significant error and needs to be compensated for. In accordance with a further aspect of the present invention, the charging time of the reference capacitor $C_R$, which will vary as a function of temperature due to variation of band-gap regulator current of approximately 1%/°C., is monitored. The change in charging time Ttemp of the reference capacitor $C_R$ is stored in the monitor 100, and used to correct for changing temperature effects.

As previously mentioned, the feature which physically responds to pressure to produce a change in pickoff capacitance is the thin diaphragm 54 in housing half member 50 created via a wire EDM process. The deflection y measured at the center of the diaphragm 54 is governed by the equation:

$$ymax = k_1(wr^4/Et^3)$$

where w is the pressure applied to one side of the diaphragm 54 (or the pressure difference), r is the width of the rectangular diaphragm 54, E is Young's Modulus for the diaphragm material, t is the thickness of the diaphragm, and $k_1$ is a constant determined by the length-to-width ratio of the diaphragm 54. In the present invention, a ratio of 2:1 was used for the sensor diaphragm 54 dimensions, yielding $k_1=0.0277$. If the ratio were reduced to 1.5:1, and width remained constant, $k_1$ would be reduced to 0.024, with a corresponding 13% reduction in diaphragm displacement. This is not a major impact on sensitivity, and shows that the length of the diaphragm 54 could potentially be reduced without a major impact on sensitivity.

In a specific construction employing the 2:1 ratio and a diaphragm thickness T of 0.0013 inches, and a gap of 0.005 inches, a baseline capacitance of approximately 3 pF was realized for both the pickoff and reference capacitors, $C_P$ and $C_R$ counting a capacitance contribution of the sensor IC chip 64. Baseline capacitance is preferably large in comparison to expected parasitic capacitances, especially those which would tend to vary over time or in response to environments, but not so large as to demand overly large charging currents. Also, the capacitances are preferably large enough to keep the oscillation frequency of the pickoff circuit around 4–6 kHz without resorting to extremely low charging currents, which would tend to decrease signal-to-noise ratio. Preliminary prediction for change in capacitance in response to pressure change is 0.5–1.5 fF/mm Hg.

The preferred embodiment of the reference and pickoff capacitors described above and depicted in the drawings, particularly FIG. 9, positions the reference capacitor plate 86 in a ring shape surrounding the pickoff capacitor plate 84 on substrate surface 61. It will be understood that the reference capacitor plate 86 may have a different shape and be positioned elsewhere on the substrate surface 61. For example, both the reference capacitor plate 86 and the pickoff capacitor plate 84 may be square or rectangular and positioned side by side on the substrate surface 61. Regardless of the configuration or position, the reference capacitor plate would be located outside the perimeter 53 of the diaphragm 54 and spaced away from the inner surface of the diaphragm 54 in the same fashion as described above. Moreover, in any such configuration, the diaphragm 54 and the pickoff capacitor plate 84 may also have a different shape, e.g. a more square shape than shown.

Pressure and Temperature Signal Modulating Circuit

Figure 10:
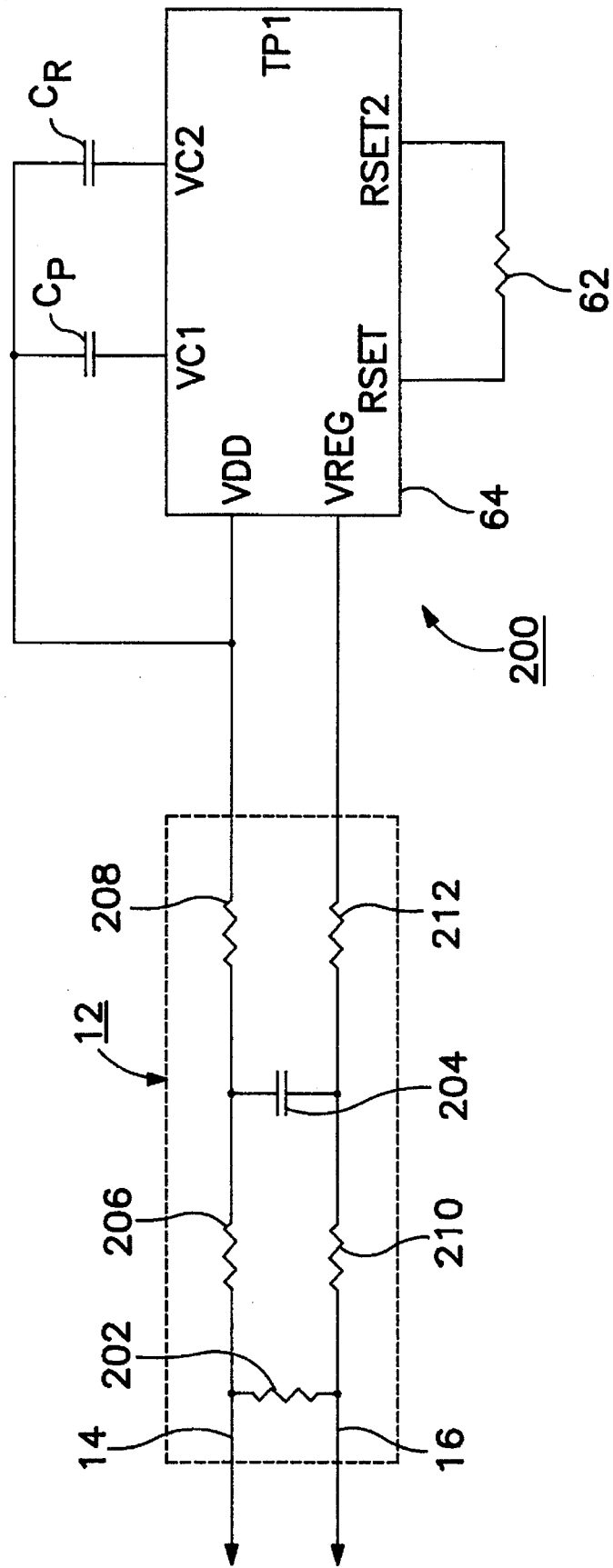
FIG. 10 is a schematic diagram of the pressure sensing lead impedance network and the pressure and temperature signal modulating circuit.
Figure 11:
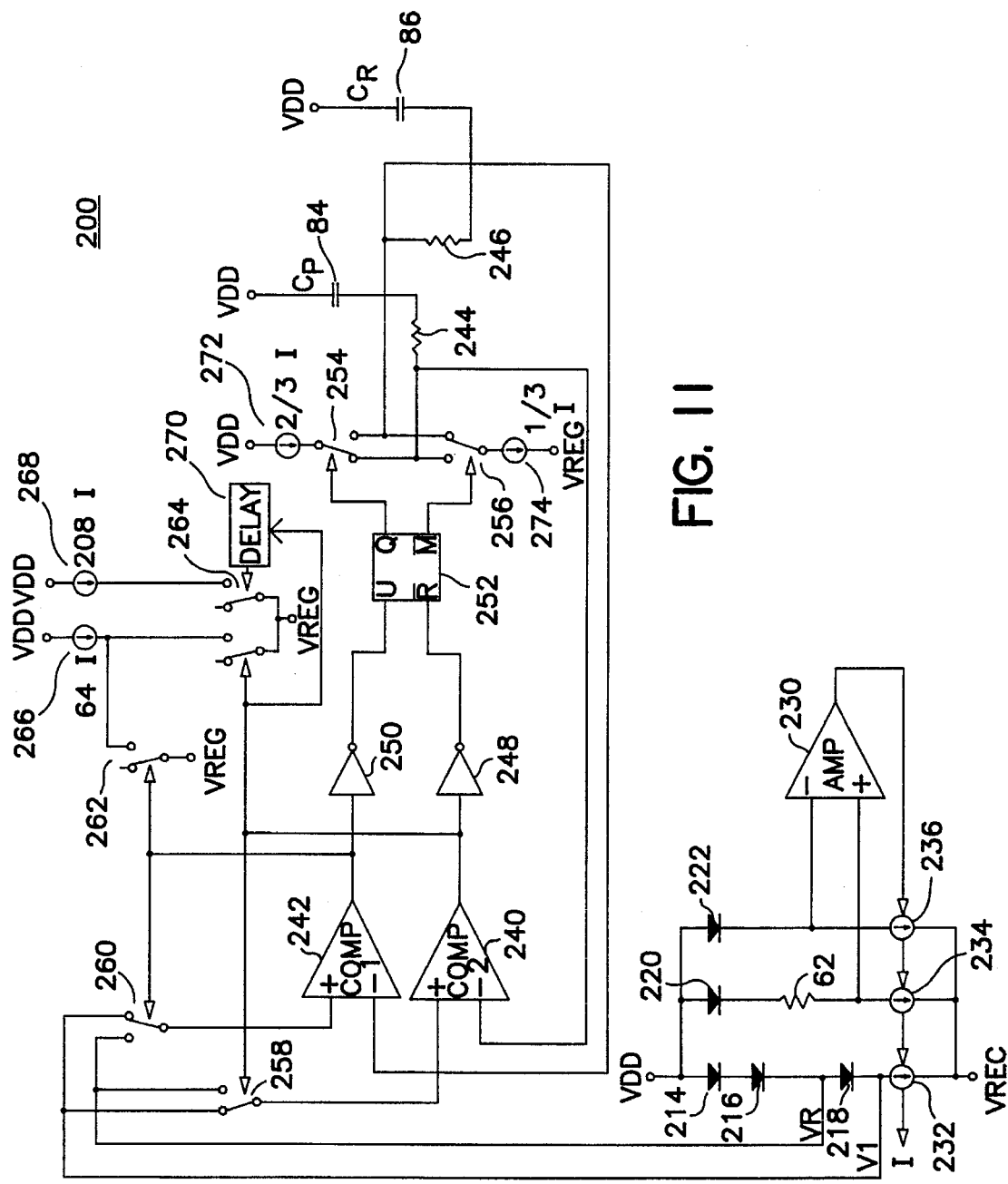
FIG. 11 is a schematic diagram of the pressure and temperature signal modulating circuit.

The pressure and temperature signal modulating sensor circuit 200 (including the circuit within the IC chip 64, the associated resistor 62 mounted on the substrate 60 and the pickoff and reference capacitors $C_P$ and $C_R$) within pressure sensing module 20 is shown in FIGS. 10 and 11. Sensor circuit 200 translates the pressure and temperature modulated pickoff and reference capacitor $C_P$ and $C_R$ values into charge time-modulated intervals Tprs and Ttemp, respectively, between sensor current pulse signals $P_R$ and $P_P$, transmitted up the active lead conductor 16.

FIG. 10 also depicts the equivalent circuit impedance of the pressure sensing lead 12 within the dotted line block denoted 12. The lead conductors 14 and 16 can exhibit a leakage resistance 202 as low as about 300 kΩ and capacitance 204 of about 110 pf between them. Lead conductor 14 has a series resistances 206 and 208 totaling about 25 Ω, and lead conductor 16 has a series resistances 210 and 212 totaling about 40 Ω. The leakage resistance and capacitance may deviate over the time of chronic implantation. The demodulator 150 includes lead load impedances and is calibrated at implantation in a manner described below.

The passive lead conductor 14 applies VDD from demodulator 150 to the VDD terminal of IC chip 64 and to the pickoff and reference capacitors $C_P$ and $C_R$. The active lead conductor 16 connects the terminal VREG of IC chip 64 to the terminals CPOUT and CPIN of demodulator 150 through an equivalent resistor network depicted in FIG. 13.

Figure 12:
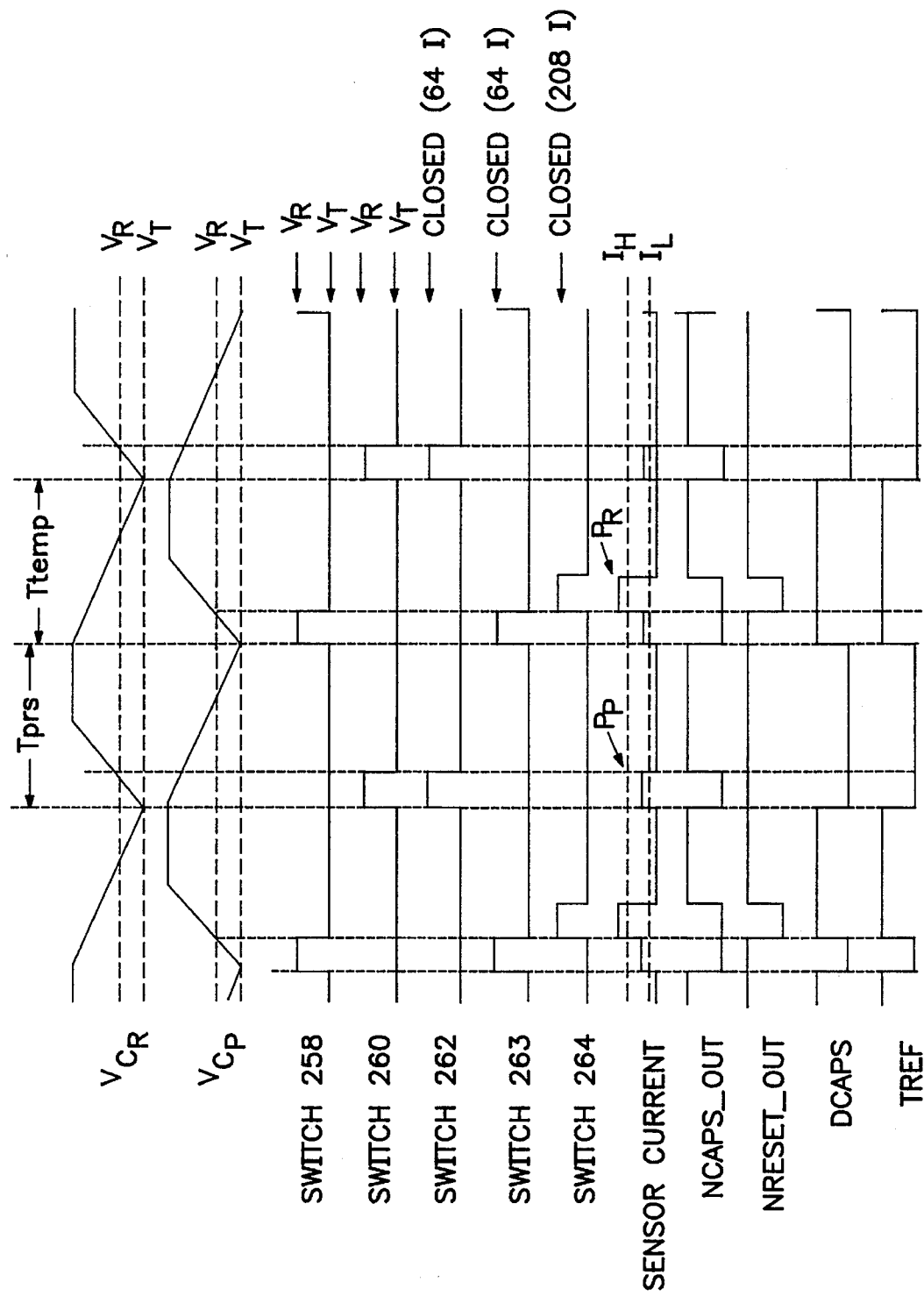
FIG. 12 is a timing diagram of the pulse signals emitted by the circuits of FIGS. 11 and 13.

The pressure and temperature signal modulating sensor circuit 200 is shown in greater detail in FIG. 11 and essentially operates as a bi-stable multivibrator operating near the target frequency of 5 kHz in alternately charging plate 86 of reference capacitor $C_R$ and plate 84 of the pickoff capacitor $C_P$ from VDD, which in this case is 0 volts, through reference voltage VR and to a target voltage VT through a current source of ⅓ I as shown in the two waveforms of FIG. 12 labeled $VC_R$ and $VC_P$. The reference capacitor $C_R$ and the pickoff capacitor $C_P$ are alternately discharged through a further current source of ⅔ I coupled to VDD through the reference voltage VR back to VDD or 0 volts as also shown in these two waveforms of FIG. 12. It should be noted that the wave forms of FIG. 12 are not to scale and are exaggerated to ease illustration of the signals generated in the sensor circuit 200 and the demodulator circuit 150.

The pickoff and reference capacitors $C_P$ and $C_R$ are both nominally 2.2 pF, but approach 3.0 pF with stray capacitances. Due to the biasing convention employed, the reference capacitor $C_R$ and the pickoff capacitor $C_P$ are considered to be discharged when their plates 86 and 84, respectively, are both at VDD or 0 volts. The common plate 51 is always at VDD or 0 volts. The reference and pickoff capacitors $C_R$ and $C_P$ are considered to be charged (to some charge level) when the plates 84 and 86 are at a voltage other than 0 volts. In this case, the charges are negative charges between VDD and VREG or between 0 and −2.0 volts. Thus, the convention employed dictates that reference and pickoff capacitors $C_R$ and $C_P$ are "charged" toward −2.0 volts and "discharged" from a negative voltage toward 0 volts. The principle involved is also applicable to a VSS convention, where the charged voltage levels would be positive rather than negative in polarity.

Figure 13:
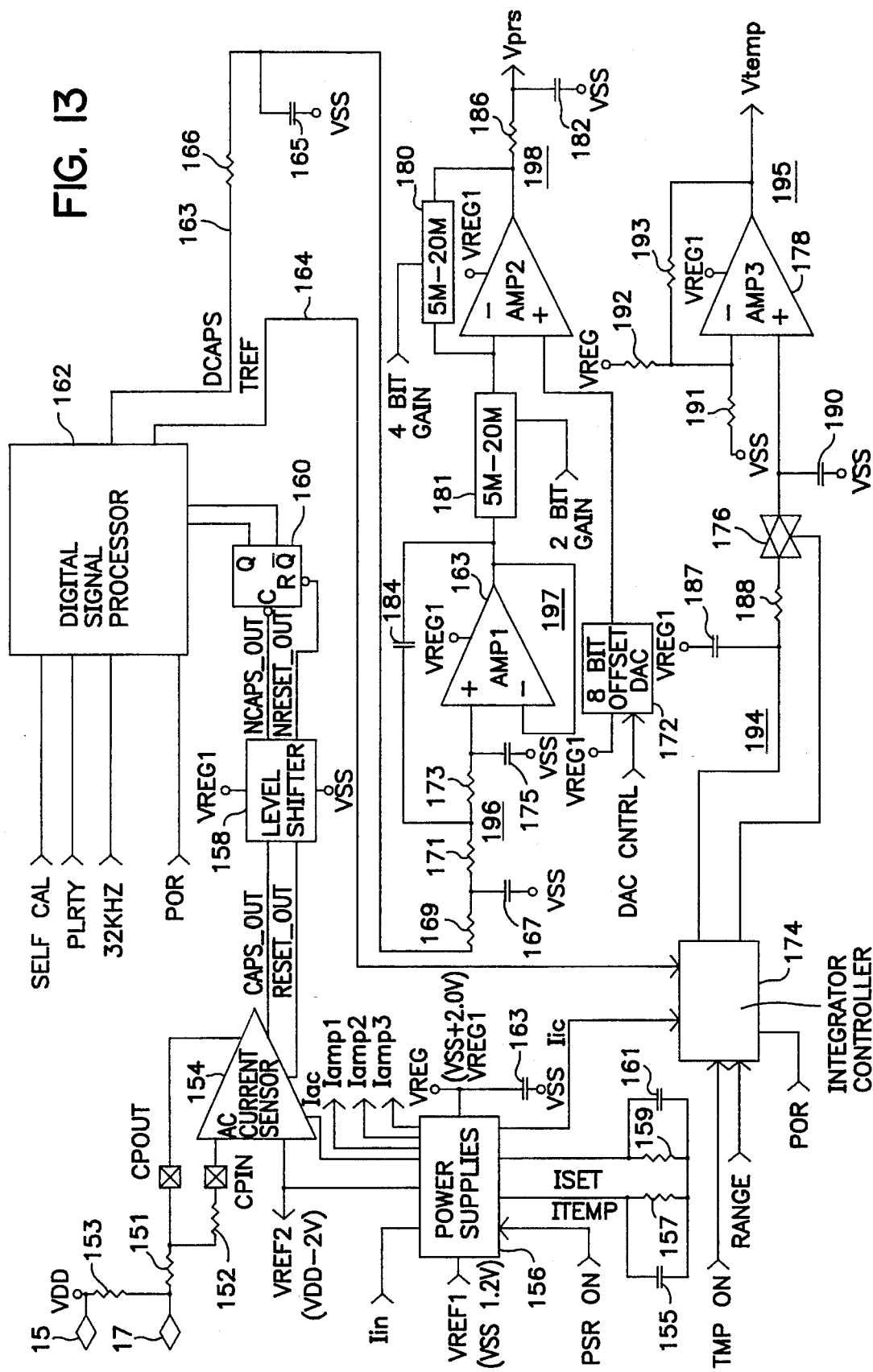
FIG. 13 is a schematic diagram of the demodulator of the pressure monitor of FIG. 1.

In practice, when demodulator 150 of FIG. 13 is powered up, it supplies the voltage VDD at 0 volts to lead conductor 14 and VREG at −2.0 volts to lead conductor 16 of the lead 12. The regulated voltages VDD and VREG supplied by the demodulator 150 to the sensor 200 of FIG. 11 are applied to a voltage dividing diode network including diodes 214, 216, and 218 and current source 232 in a first branch, diode 220, external resistor 62, and current source 234 in a second branch, and diode 222 and current source 236 in a third branch. Voltage VT is three diode forward voltage drops lower than VDD through diodes 214, 216 and 218, or about −1.5 volts, and voltage VR is two diode forward voltage drops lower than VDD through diodes 214 and 216 or about −1.0 volts.

Differential current amplifier 230 is coupled to the second and third branches and its output is applied to current sources 232, 234 and 236 in each branch. The current I is defined by the voltage difference between two diodes 220 and 222 operating at significantly different current densities, divided by the value of the chip resistor 62. Changes in ambient temperature affect the diode resistances and are reflected in the output signal from differential amplifier 230.

Current sources 234, 236 are driven to correct any current imbalance, and current source 232 develops the current I reflecting the temperature change within the sensor module 20.

The principle employed in the pressure and temperature signal modulating sensor circuit 200 is a deliberate misuse of the band gap regulator concept, in that rather than using the band gap method to create a current source insensitive to temperature, the current source 232 varies a known amount, about 1%/°C., with variation in temperature. This allows the variation in the reference capacitor $C_R$ charge-modulated time Ttemp to be used as a thermometer, in the interest of correcting for sensor internal pressure change with temperature and subsequent absolute pressure error affecting the gap, and hence the capacitance, of the pickoff capacitor $C_P$. Since the gap of the reference capacitor $C_R$ cannot change significantly with pressure or temperature, the primary change in Ttemp can only occur due to temperature induced change in current I generated by current source 232.

The reference voltage VR and the target voltage VT are applied to the switched terminals of schematically illustrated semiconductor switches 258 and 260. The common terminals of semiconductor switches 258 and 260 are coupled to a positive input of comparators 240 and 242, respectively. The negative terminals of comparators 240 and 242 are coupled through the series charge resistors 244 and 246, respectively, to the plates 84 and 86 of the pickoff capacitor $C_P$ and the reference capacitor $C_R$, respectively.

The outputs of the comparators 240 and 242 are inverted by inverters 248 and 250, respectively, and applied to inputs of the flip-flop 252. The outputs of the flip-flop 252 are applied to control terminals of the schematically illustrated semiconductor switches 254 and 256. Semiconductor switches 254 and 256 are bistable in behavior and alternately connect current source 272, providing ⅔ I, and current source 274, providing ⅓ I, to the reference capacitor $C_R$ and the pickoff capacitor $C_P$ depending on the state of flip-flop 252. When the current source 272 is applied to one of the capacitors, the current source 274 is applied to the other capacitor. The capacitor voltage on plate 84 or 86 is discharged through current source 272 back to VDD or 0 volts while the capacitor voltage on plate 86 or 84, respectively, is charged through current source 274 toward VT as shown in FIG. 12.

The outputs of comparators 240 and 242 are also applied to control the states of schematically illustrated semiconductor switches 258, 260, 262, 263 and 264. Semiconductor switches 258 and 260 are monostable in behavior and switch states from the depicted connection with target voltage VT to reference voltage VR each time, and only so long as, a high state output signal is generated by the respective comparators 240 and 242. The timing states of these switches 258 and 260 closed for conducting VR or VT to respective comparators 240 and 242 are also shown in the wave forms labeled 258 and 260 shown in FIG. 12.

The outputs of comparators 240 and 242 are normally low when the capacitor charge voltages $VC_P$ and $VC_R$, respectively, applied to the positive terminals are lower, in an absolute sense, than the voltages VT applied to the negative terminals. The charging of the capacitor $C_P$ or $C_R$ coupled to the charge current source 274 to the voltage VT or −1.5 volts causes the associated comparator 240 or 242 to go high. When the comparator goes high, the flip-flop 252 changes state exchanging the closed states of semiconductor switches 254 and 256, thereby causing the previously charging (or fully charged) capacitor to commence discharging and causing the previously discharged other capacitor to commence charging.

The high output state of the associated comparator remains for a predetermined capacitor discharge time period from VT to VR providing a one-shot type, high state output. When the capacitor $C_P$ or $C_R$ voltage discharges to VR, the high state output of the respective comparator 242 or 240 is extinguished, and semi-conductor switches 258 or 260 is switched back to apply VT to the respective negative terminal of the comparator 240 or 242. However, the capacitor $C_P$ or $C_R$ continues to discharge until the plate 84 or 86, respectively, is back at full discharge or 0 volts. Since the discharge rate exceeds the charge rate, there is a period of time in each cycle that the capacitor $C_P$ or $C_R$ remains at 0 volts while the other capacitor charges toward VT (as shown in FIG. 12). This ensures that each capacitor is fully discharged to 0 volts at the start of its respective charge time interval.

As shown specifically in FIG. 11, the switches 258 and 260 are set to apply the voltage VT to comparators 240 and 242, and the switches 262, 263 and 264 are all open. The plate 84 of pickoff capacitor $C_P$ is connected with the ⅔ I current source 272 and is being discharged toward VDD, that is 0 volts, while the plate 86 of reference capacitor $C_R$ is connected with the ⅓ I current source 274 and is being charged toward VT or −1.5 volts. Because of the arrangement of the switches, 258, 260, 262, 263, and 264, no pulses are being generated. It can be assumed that the plate 84 of pickoff capacitor $C_P$ is being charged from VDD toward VR and that the voltage on the plate 86 of reference capacitor $C_R$ is discharging from VR toward VDD. When the output of comparator 242 does go high, the high state signal will cause switch 260 to switch over from the then closed pole position (e.g. the pole position schematically depicted in FIG. 11) to the other open pole position and remain there until the comparator 242 output goes low again when the capacitor voltage falls back to VT. Similarly, when the output of comparator 240 goes high in the following charge cycle, the high state signal causes switch 258 to switch over from the then closed pole position (e.g. the pole position schematically depicted in FIG. 11) to the other pole position and remain there until the comparator 240 goes low. In this fashion, the reference voltage VR is alternately applied by switches 258 and 260, respectively, to the negative terminals of comparators 240 and 242 for the relatively short VR to VT discharge times shown in FIG. 12.

To summarize, when the charge voltage on the pickoff capacitor $C_P$ reaches VT, the comparator 240 switches its output state high, in turn changing the state switch 258 and closing switch 263. Delay circuit 270 is enabled to close switch 264 when switch 263 re-opens. Similarly, in the next cycle, when the voltage on reference capacitor $C_R$ reaches VT, the comparator 242 switches its output state high, changing the state of switch 260 and closing switch 262.

Normally open semiconductor switches 262 and 263 are also monostable in behavior and are closed for the duration of the comparator high state, that is, the VT to VR discharge time period. When closed, the timing current pulses $P_R$ and $P_P$ separating (at their leading edges) the reference and pickoff charge-time modulated intervals Ttemp and Tprs also shown in FIG. 12 are generated.

The timing current signal pulse $P_P$ is controlled in width by the reference capacitor $C_R$ capacitor discharge time from VT to VR as shown in the Sensor Current line of FIG. 12. The initial low amplitude step of two step timing current signal pulse $P_R$ is also controlled in width by the reference capacitor $C_R$ capacitor discharge time from VT to VR as shown in the wave form labeled Sensor Current in FIG. 12. The VT to VR discharge times, which govern the closed time periods of switches 258 and 260 and the widths of the low amplitude steps of the timing current pulses $P_R$ and $P_P$, are nominally 8–12 μsec. The high amplitude step of two step timing current signal pulse $P_R$ is controlled in width by delay circuit 270 of FIG. 11.

The high state signal output of comparator 242 therefore closes normally open switch 262 for the duration of the high state, i.e. the VT to VR discharge time of reference capacitor $C_R$. When switch 262 closes, the current source 266 providing 64 I is applied to the VREG terminal, resulting in the generation of the timing current pulse $P_P$ depicted in FIG. 12 appearing on conductor 16 as a sensor current. Similarly, the high state signal output of comparator 240 also closes the normally open switch 263 for the VT to VR discharge time of duration of pickoff capacitor $C_P$ and is applied to the delay circuit 270. Delay circuit 270 effects the closure of switch 264 at the end of the high state and then maintains closure of the switch 264 through a delayed high state time period. When switches 263 and 264 are sequentially closed, the current source 266 providing 64 I is applied to the VREG terminal, and then the current source 268 providing 208 I is applied to the VREG terminal. In this manner, the stepped current timing pulse $P_R$ depicted in FIG. 12 is generated.

The nominal pulse height of 8.0 μA for timing current pulse $P_P$ and for the initial step of timing current pulse $P_R$ is effected by the 64 I current source 266 when either switch 262 or 263 is closed. The nominal, pulse height of 24.0 μA (stepped up from the initial 8.0 μA step) of pulse $P_R$ is effected by the 208 I current source when switch 264 is closed after switch 263 reopens. Between pulses, a baseline supply current of 1.5 μA is present at VREG and on lead conductor 16 to which the current pulse heights or sensor current amplitudes are referenced.

The 8.0 μA leading step of pressure-related timing current pulse $P_P$ matches the slew rate of the 8.0 μA peak of temperature-related, reference timing current pulse $P_R$, which reduces errors that would otherwise be associated with detection of different amplitude pulses having differing slew rates. The rise time of both of the pulses appears to be the same to the current sensor 154 in the demodulator 150. The start of each pulse can therefore be accurately detected and employed as the start and end times for the intervening charge time intervals Tprs and Ttemp. The differing peak amplitudes of the two pulses are readily distinguishable to determine the order of the intervals.

Thus, FIG. 12 illustrates the waveforms at the switches 258, 260, 262, 263 and 264 in relation to the charge and discharge voltage waveforms of the reference and pickoff capacitor $C_R$ and $C_P$ as well as the timing current pulses $P_P$ and $P_R$ generated at the terminal VREG marking the starts of the respective capacitor charging intervals Tprs and Ttemp.

At 37° temperature and a barometric pressure of 740 mm Hg, the capacitance values of capacitors $C_P$ and $C_R$ are approximately equal. Therefore, both capacitors $C_P$ and $C_R$ charge at an approximately equal rate. The intervals between timing signal pulses $P_P$ and $P_R$ are approximately equal, reflecting a 50% duty cycle (calculated as the ratio of Tprs to Ttemp+Tprs), and the nominal operating frequency from $P_P$ to $P_P$ is 5 kHz.

After implantation, the temperature should vary somewhat from 37°. The current I, which changes with temperature change, affects the charge times Ttemp and Tprs equally which changes the operating frequency. In addition, the blood pressure change between systole and diastole alters the capacitance of the pickoff capacitor $C_P$ which only affects the charge time Tprs. Thus, charge time Ttemp only changes with temperature, and the combined result is a change in frequency and duty cycle dependent on both temperature and pressure changes.

The schematically illustrated current sources and semiconductor switches may be readily realized with conventional integrated circuit designs.

Demodulator Circuit

The demodulator 150 shown in FIG. 13 supplies the voltages VDD and VREG, at a baseline current drain from sensor IC chip 64 of about 1.5 μA, to the lead conductors 14 and 16 and receives the timing signal current pulses $P_P$ and $P_R$ modulating the baseline current on conductor 16. The demodulator 150 converts the charge time intervals Tprs and Ttemp separating the leading edges of the train of current pulses of FIG. 12 into voltage signals Vprs and Vtemp, respectively. The voltage signals Vprs and Vtemp are supplied to the digital controller/timer circuit 132 and are converted by ADC/MUX circuit 142 into digital values representing absolute pressure and temperature data, which are stored in the microcomputer circuit 114 in a timed relationship with other monitored physiologic data.

As described above, the analog temperature signal Vtemp is derived from the interval Ttemp between the leading edges of $P_R$ and $P_P$ in an integration process, and the analog pressure signal Vprs is derived from the interval Tprs between the leading edges of $P_P$ and $P_R$ in a duty cycle signal filtering and averaging process. In these processes, the demodulator 150 creates the intermediate voltage square waves NCAPS_OUT, NRESET_OUT, and DCAPS shown in FIG. 12 from the current pulse timing intervals. The voltage signal Vtemp can be determined from a relatively simple integration of a time interval related to the time interval Ttemp. The voltage signal Vprs is derived by low pass filtering the square waves of the DCAPS signal representing the time intervals Tprs and Ttemp to obtain the average voltage.

The temperature related capacitance changes are specified to be in a narrow range of 37° C.±5° C. which could effect an ideal gas law pressure variation of 20 mm Hg full scale over the 10° C. temperature change. The limited range of the A/D conversion provided by the ADC/MUX circuit 142 and the trimmed slope of the temperature channel integrator causes a Ttemp to range between 66 μsec to 116 μsec in a first range and between 96.5 μsec to 146.5 μsec in a second range. The resulting voltage range of the analog signal Vtemp produced at the output of the temperature processing channel is specified to be from 0 to 1.2 volts to be processed by the ADC/MUX circuit 142.

The blood, ambient (atmospheric, altitude, meteorologic) pressure changes affecting the pickoff capacitor are specified in a preferable total range of 400 to 900 mm Hg. The DAC offset adjustment allows the pressure system to be adjusted under user and/or software control to provide this total range in order to be compatible with the more limited range of the 8 bit A/D convertor.

In practice the gain of the pressure system will be adjusted dependent on the sensitivity of the particular pressure sensor in order to provide an A/D pressure "range" that encompasses the expected blood pressure range of the patient plus expected local meteorologic pressure changes and expected altitude pressure changes seen by the patient. The blood pressure is normally expected to be −10 mm Hg to 140 mm Hg of gauge pressure (relative to ambient).

The resulting voltage range of the analog signal Vprs produced at the output of the absolute pressure signal processing channel is also specified to be from 0 to 1.2 volts to be processed by the ADC/MUX circuit 142.

Turning again to the demodulator circuit 150 of FIG. 13, it receives a number of biasing and command signals from the digital controller/timer circuit 132, supplies the voltages VDD and VREG to the pressure and temperature signal modulating circuit 200, processes the sensor current pulses $P_R$ and $P_P$, and provides the analog signals Vtemp and Vprs to the digital controller/timer circuit 132. Commencing first with the biasing and operating input signals, the demodulator circuit 150 receives the regulated voltage signal VREF1 at +1.2 volts, a current signal Iin of 20 nA, and a command signal PSR ON at the power supply 156. The regulated voltage VREF1 is the same reference voltage as is employed by the ADC/MUX circuit 142 for digitizing the analog voltage signal between 0 and +1.2 volts into an 8-bit digital word having 0–255 values. The output signals Vprs and Vtemp therefore must fall in this range of 0–1.2 volts to be processed. It is simpler then to develop accurate regulated voltages and currents of the demodulator 150 from that same regulated voltage. In addition, it should be noted that the demodulator circuit 150 as well as the other circuits of the monitor 100 including the microcomputer circuit 114 are referenced to VSS or battery ground which is at 0 volts. Therefore, the conventions are reversed from those prevailing in the sensor circuit 200. It will be understood that the same convention could be used in both cases.

From this source, the power supply 156 develops the voltage VREF2 at –2.0 volts below VDD (VDD–2.0 volts), VREG1 at +2.0 volts, and the regulated current signals Iac, Iamp1, Iamp2, Iamp3, and Iic that are applied to the circuit blocks of FIG. 13. The off-chip capacitor and resistor networks 155, 157 and 159, 161 provide bias controls ITEMP for the current Iic and ISET for the current Iac, respectively. The resistor 159 is selected to provide the Iac current to develop specific current thresholds described below for the AC current sensor 154. The resistor 157 is trimmed at the manufacture of each monitor 100 to provide a specific current level Iic for the integrator controller 174.

The POR and 32 kHz clock signals are applied on power-up of the monitor 100. The command signal PSR ON, and other command signals TMP ON, 2-BIT GAIN, 4-BIT GAIN, 8-BIT DAC CNTRL, SELF CAL, PLRTY and RANGE are provided to the demodulator circuit 150 by the digital timer/controller circuit 132 from memory locations within the microcomputer circuit 114. Programmed-in commands dictate the operating states and parameters of operation reflected by these command signals. Command signal values and states are stored in microcomputer 114 in memory locations that are accessed from the digital timer/controller circuit 132 and supplied to the demodulator circuit 150 in three words. A GAIN word of 6 bits (2-BIT GAIN & 4-BIT GAIN), a DAC word of 8 bits and a CONTROL word of 6 bits (POR, PSR ON, TMP ON, SELF CAL, RANGE, PLRTY) are stored to set the operating states and selected parameters of operation.

For example, the pressure and temperature sensing functions can be separately programmed ON or OFF or programmed ON together by the PSR ON and TMP ON signals. The 1-bit PSR ON command enables the bias currents Iamp1, Iamp2, Iamp3 to operate the pressure signal processing channel. The 1-bit TMP ON command enables the integrator controller 174 to operate the temperature signal processing channel. The remaining command values and states will be explained in context of the components of the demodulator circuit 150.

Turning to the processing of the sensor current pulses $P_P$ and $P_R$, the lead conductor 14 is connected to the connector block terminal 15 which is also connected to VDD. The lead conductor 16 is connected to the VREG connector block terminal 17. A load resistor 153 is coupled across connector block terminals 15 and 17 and between VDD and VREG in order to obtain a 2.0 volt drop and to reduce the effects associated with changes in the lead leakage resistance 202. The lead conductor 16 at connector block terminal 17 is connected through resistors 151 and 152 to one input terminal CPIN of the AC current sensor 154 and through resistor 151 alone to the output terminal CPOUT connected to a current sink in the AC current sensor 154.

A further input terminal of AC current sensor 154 is connected to the voltage VREF2 at (VDD–2.0) volts developed by power supply 156. The current sensor 154 operates as a voltage regulator for ensuring that the voltage at CPOUT remains at VREF2 or (VDD–2.0) volts at all times, regardless of the effect of the current pulses $P_P$ and $P_R$ generated during charge of the capacitors $C_P$ and $C_R$ as described above and appearing on conductor 16 at connector block terminal 17. Since the voltage drop across resistor 151 is small, VREG of the circuit 200 in FIG. 11 may be viewed as VREF2 of the demodulator circuit 150 of FIG. 13. Resistor 151 provides protection against external overdrive due to electromagnetic interference or cardioversion/defibrillation pulses.

The current sensor 154 also includes comparators established by the current Iac that discriminate the amplitudes of current pulses $P_P$ and $P_R$ when they appear and generate the output signals CAPS_OUT and RESET_OUT. The signal amplitudes are discriminated and reduced to current levels established by the comparators and reference current sources in AC current sensor 154. The CAPS_OUT signal is developed in response to both of the low and high amplitude current pulses $P_R$, and the RESET_OUT signal is developed in response to the high amplitude current pulse $P_R$ only.

The discrimination of the distinguishing parameters of the current pulses $P_P$ (8.0 µA) and $P_R$ (8.0 µA followed by 24.0 µA) is effected by amplitude comparators in AC current sensor 154 that are set by current Iac provided by power supplies 156. The resistor 159 determines the current ISET which in turn determines the current Iac and the thresholds for the input current pulses in the AC current sensor 154. Preferably, a low current threshold $I_L$ of +3.6 µA and a high current threshold $I_H$ of +14.4 µA are established for the 8.0 µA and 24.0 µA nominal current pulse amplitudes. The ratio of these two thresholds cannot be changed, but their values are set by resistor 159 to allow for variances in the actual peak step amplitudes of the current pulses $P_P$ and $P_R$.

A sensor current pulse $P_P$ or $P_R$ having a step that exceeds the $I_L$ (+3.6 µA) low threshold generates an output signal at CAPS_OUT, whereas the high step of current pulse $P_R$ that exceeds the $I_H$ (+14.4 µA) high threshold generates an output signal at RESET_OUT. The CAPS_OUT and RESET_OUT signals are applied to the level shifter 158 which responds by normalizing the signals between VSS or 0 volts and VREG1 of +2.0 volts and providing the NCAPS_OUT and NRESET_OUT signals shown in FIG. 12. The normalized NCAPS_OUT and NRESET_OUT signals are applied to the clock and reset inverting inputs, respectively, of flip-flop 160. The inverting inputs effectively invert the depicted NCAPS_OUT and NRESET_OUT signals shown in FIG. 12. The flip-flop 160 responds by providing a square wave output signal CAPS (not shown in FIG. 12) at its Q-output that is high during the interval Tprs and low during the interval Ttemp.

In the decoding of the Ttemp and Tprs intervals from the current pulse peaks $P_P$ and $P_R$, the NCAPS_OUT signal is applied to inverting clock input of flip-flop 160 to cause it to switch state. The NRESET_OUT signal is applied to the inverting reset input of flip-flop 160 and does not cause it to change state when its state at the Q output is already low. If, however, the Q output state is high on arrival of NRESET_OUT, the flip-flop 160 state is switched low, resulting in the high state of the DCAPS square wave signal as shown in the first instance in FIG. 12. The high amplitude phase of current pulse $P_R$ therefor synchronizes the state of the DCAPS square wave signal on power up and restores any loss of synchronization that may occur from time to time. Once synchronization is established, each successive 8 μA step of the respective current pulse peaks $P_P$ and $P_R$ shown in FIG. 12 switches the Q output state of the flip-flop 160, causing the square wave of the CAPS and DCAPS signals reflecting the Ttemp and Tprs intervals.

The CAPS square wave output signal is applied to a digital signal processor 162 and is normally inverted to provide the DCAPS signal shown in FIG. 12 at a first output. The digital signal processor 162 also normally inverts the CAPS signal to provide the TREF signal at a second output. In this fashion, the Tprs interval of DCAPS provided to the input of pressure signal processing channel 163 is negative in polarity, and the Ttemp interval of TREF provided to the input of the temperature signal processing channel 164 is positive in polarity. In regard to the polarities of signals DCAP and TREF, the digital signal processor 162 also receives the PLRTY signal from the digital controller/timer circuit 132. The PLRTY signal may be selectively programmed to invert the polarity of the DCAPS square wave in order to increase the operating range of the pressure signal processing channel 163. However, it is expected that the PLRTY signal would seldom be changed, and such a programming option may be eliminated if the range provided in the pressure signal processing channel 163 is sufficient.

As described further below, a self calibration mode can be initiated in response to a SELF CAL signal to apply a 5.46 kHz square wave signal through the digital signal processing circuit 162 to the temperature integrator controller 174 for calibration purposes. The 5.46 kHz square wave signal is simply chosen for convenience, since it is an even submultiple of the 32 kHz clock frequency and is close to the nominal 5 kHz operating frequency. The following discussion assumes first that the temperature processing channel 164 is already calibrated in the manner described below and that the normal operating mode is programmed (SELF CAL off) so that only the CAPS signal is processed by the digital signal processor 162.

Addressing the derivation of the signal Vtemp by the temperature signal processing channel 164 first, the temperature is demodulated from the high state of the TREF square wave signal having a duration directly relating to the charge time Ttemp. The integrator controller 174 employs the current Iic to charge an integrator capacitor 187 over the time Ttemp (or a portion of that time as explained below) and then charges sample and hold capacitor 190 to the voltage on integrator capacitor 187. The voltage on integrator capacitor 187 is then discharged and the voltage on sample and hold capacitor 190 is amplified by temperature amplifier stage 195 to become the Vtemp signal in the range of 0–1.2 volts.

More particularly, when the integrator capacitor 187 is not being charged or the voltage transferred to the sample and hold capacitor 190, both plates of the integrator capacitor 187 are held at VREG1 and the bidirectional switch 176 is open. Again, the discharge state is characterized as a state where there is no net voltage or charge on the capacitor 187, and the charged state is characterized by a net voltage difference across its plates, even though the "charged" voltage may be nominally lower than the "discharged" voltage.

When the TREF signal goes high (and the low range is programmed), the integrator controller 174 commences charging the plate of integrator capacitor 187 connected to resistor 188 to a voltage lower than VREG1 through a current sink to VSS internal to integrator controller 174. At the end of the high state of the TREF signal, the current sink to VSS is opened and the bidirectional switch 176 is closed for one clock cycle time (30.5 μsec) to transfer the resulting voltage level on capacitor 187 to capacitor 190. Bidirectional switch 176 is then opened, and capacitor 187 is discharged by setting both plates to VREG1 through switches internal to integrator controller 174. With each successive recharge of integrator capacitor 187, the capacitor 187 voltage level achieved varies upward and downward from its preceding voltage level with changes in the width of the high state of the TREF signal, and the new voltage level is transferred to capacitor 190. The new voltage level is held on capacitor 190 when the switch 176 is opened.

The switching of bidirectional switch 176, resistor 188 and capacitor 190 also form a low pass filter. The pass band of this filter is sufficient to allow only the temperature related component of the signal to pass through and be reflected on capacitor 190.

The resulting voltage on capacitor 190, amplified by amplifier stage 195, provides the Vtemp signal representing the temperature in the pressure sensor cavity. Amplifier stage 195 includes an amplifier 178 referenced back to approximately +1.2 V through the voltage divider comprising resistors 191, 192, 193 dividing the VREG1 of +2.0 volts. Amplifier stage 195 has a gain of two, and so the maximum voltage which the sample and hold capacitor 190 can reach is +0.6 V. This corresponds to a +0.6 volt level on integrating capacitor 187 at its junction with resistor 188 which is achieved in 116 μsec employing the regulated current Iic.

Two operating ranges provide a higher resolution of the possible values of the reference capacitor $_R$ charging time Ttemp reflected by the high state of the TREF signal. Either a high or low range must be programmed by the RANGE bit based on individual sensor circuit 200 characteristics and/or the temperature range of the patient. Since a 5° C. change in temperature will result in approximately 5% change in Ttemp, the 8-bit ADC count provided by ADC/MUX circuit 142 in response to Vtemp for a particular lead cannot be near the limits of 0 and 255.

For this reason, both the high range and low range for the temperature are provided, and one or the other is selected via a one-bit value of the above-referenced 6-bit CONTROL word. Setting the RANGE bit to 1 places integrator controller 174 in the high range mode which corresponds to a TREF high state pulse width of 96–146 μsec. Programming the RANGE bit to 0 places integrator controller 174 in the low range mode which corresponds to a TREF high state pulse width of 66–116 μsec. The limit of 0.6 volts can be reached at the upper end of this pulse width range.

However, it is anticipated that the high operating range will be necessary in certain instances. When the high range mode is selected, the integrator controller 174 effectively prolongs the high state TREF square wave by delaying the charging of the integrator capacitor 187 by one clock cycle or 30.5 μsec from the beginning of the high state TREF square wave. This effectively shortens the TREF high state pulse width range of 96–146 μsec that is integrated back to 66–116 μsec, allowing the Vtemp voltage signal to fall into the 0–0.6 volt range that can be doubled in amplifier stage 195, digitized and stored. The programmed range is also stored with the digitized temperature data so that the proper values can be decoded from the telemetered out data.

In order to set the RANGE for proper temperature measurement in a given patient, one or the other range is programmed and the digitized temperature readings are accumulated and telemetered out. If they are in a proper range, then the programmed RANGE is correct. In general, if in the low range mode and if the digital temperature value is a digital word 50 or less, it is necessary to program the high range. And, if in high range mode and the digital word is 200 or more, it is necessary to program to the low range. Alternatively, the range could be automatically switched at these threshold levels.

The rate of charge of integrator capacitor 187 in these ranges to get to the proper voltage range of 0–0.6 volts depends on the current Iic. The self calibration of the temperature signal processing channel 164 is necessary to trim the resistor 157 to precisely set the current ITEMP and the current Iic so that a voltage of 0.590 volts is reached on capacitor 187 after a 116 μsec integration time. In this mode, the RANGE is programmed to the low range, and the SELF CAL signal is programmed ON. The digital signal processor 162 responds to the SELF CAL ON signal to divide the 32 kHz clock signal provided from digital controller/timer circuit 132 by 6 into a 5.46 kHz square wave signal exhibiting a 50% duty cycle. The digital signal processor substitutes the square wave calibration signal for the TREF signal and applies it to the temperature signal processing channel 164 and to the input of the integrator controller 174. The resistance of resistor 157 is trimmed to adjust integrator current Iic until the voltage 0.590 volts is achieved in 116 μsec or an ADC count of 125 is reached.

Turning now to the derivation of the pressure signal Vprs, the nominally 5 kHz DCAPS positive and negative square wave of +2.0 volts is filtered and averaged to derive a voltage signal Vprs in the range of 0–1.2 volts at the junction of capacitor 182 and resistor 186. The 5 kHz signal component is filtered out by a 4-pole filter including a 250 Hz low pass filter provided by capacitor 165 and resistor 166, an active Butterworth filter comprising 40 Hz low pass filter network 196 and first pressure amplifier stage 197, and a further 1 pole, 250 Hz low pass filter pole comprising capacitor 182 and resistor 186. The low pass filter network 196 comprises the resistors and capacitors 165–167, 169, 171, 173, 175, 182 and 186 and averages the voltage square wave to create a D.C. voltage proportional to the DCAPS square wave signal duty cycle. The first pressure amplifier stage 197 buffers the filtered pressure-related signal at its output. The filtered output signal is applied to second, inverting, pressure amplifier stage 198 which comprises the amplifier 170 and the programmable gain, switched resistor networks 180 and 181. Amplification and voltage offset of the output signal of amplifier 168 is provided in second pressure amplifier stage 198 by the 2-BIT GAIN, 4-BIT GAIN and 8-bit offset DAC settings.

The variations in the manufacturing tolerances and conditions of the sensor module 20 affects the reference and pickoff capacitance values and the response to temperature and pressure changes that particularly affect the pressure sensing function. The gain and offset adjustments are provided to correct for such affects. The offset adjustment is also required to provide for pressure range adjustments so that the pressure range used provides adequate resolution of pressure differences. As mentioned above, the A/D conversion range of the ADC/MUX circuit 142 is limited to 256 digitized values from a voltage range of 1.2 volts. Therefore, it is necessary to compensate for variations in the patient's own blood pressure range as well as prevailing atmospheric pressure primarily related to the altitude that the patient normally is present in. These compensations are included in an offset factor developed at the time of implant.

The offset factor is provided by the 8-bit offset digital to analog converter (DAC) 172 which provides an offset analog voltage dependent on the programmed value of the DAC CNTRL binary coded digital word. The primary function of the DAC 172 is to provide the analog voltage to "zero" the offset in the system in order to keep the pressure signal within the range of the ADC/MUX block 142 (0–1.2 volts). The analog offset voltage is applied to differential pressure amplifier 170 where it is subtracted from the output voltage of the first pressure amplifier 168. The total programmable range of the DAC 172 is 630 mV, between 570 mV to 1,200 mV.

The gain settings for the second pressure amplifier stage 198 can be adjusted by programming values for the 4-BIT GAIN and 2-BIT GAIN binary words stored in the RAM 124 of FIG. 1 by the external programmer. The 4-BIT GAIN signal controls the gain of the pressure amplifier stage 198 by setting switched resistors in feedback switched resistor network 180 to the binary coded gain word to provide a gain range that is selectable by the further 2-BIT GAIN signal setting of switched resistor network 181. The gain setting can be varied from 5 X–20 X in 1 X increments, 10 X–40 X in 2 X increments and 20 X–80 X in 4 X increments. The gain ranges and increments are established by the 2-BIT GAIN control signal applied to the series switched resistor network 181.

The first pressure amplifier stage 197 responds to the ratio of Ttemp to the sum of Ttemp and Tprs resulting in a first filtered voltage signal. The second pressure amplifier stage 198 amplifies and inverts the first voltage signal as a function of the offset and gain settings and therefore responds effectively to the ratio of Tprs to the sum of Ttemp and Tprs, or the duty cycle of Tprs. The output signal from amplifier 170 of the second amplifier stage 198 is applied to a further low pass filter stage comprising resistor 186 and capacitor 182 to filter out any remaining component of the about 5 kHz oscillation frequency and/or any noise. The resulting filtered signal is applied as pressure signal Vprs to the digital controller/timer circuit 132 of FIG. 1.

The resulting Vprs and Vtemp voltage signals are digitized in the ADC/MUX circuit 142 in a manner well known in the art to provide digitized Vprs and Vtemp data values. The digitized Vprs and Vtemp data values are applied on bus 130 to the microcomputer circuit 114 for storage in specified registers in RAM/ROM unit 128. The digitized Vtemp data value may be employed in processing the digitized data values telemetered out by the external programmer to compensate for the temperature induced affects on the Vprs data values. The stored data values may also be correlated to data from the activity sensor block 152 and other sensors, including other lead borne sensors for monitoring blood gases and the patient's EGM as described above.

The capacitive pressure and temperature sensing system described above is intended for implantation in the body of a patient. However, it will be understood that the sensor lead 12 may be implanted as described above through a venous approach but with its proximal connector end coupled through the skin to an external system 100 for ambulatory or bedside use. In addition, the system 100 may be simplified to the extent that the data may be transmitted remotely in real time to an external programmer/transceiver instead of being stored in microcomputer circuit 114. In the latter case, the microcomputer circuit 114 may be eliminated in favor of a more limited, digital discrete logic, programming command memory of types well known in the prior art of pacing.

Variations and modifications to the present invention may be possible given the above disclosure. Although the present invention is described in conjunction with a microprocessor-based architecture, it will be understood that it could be implemented in other technology such as digital logic-based, custom integrated circuit (IC) architecture, if desired.

It will also be understood that the present invention may be implemented in dual-chamber pacemakers, cardioverters, defibrillators and the like. However, all such variations and modifications are intended to be within the scope of the invention claimed by this letters patent.

PARTS LIST FOR FIGS. 1–13 patient's heart 10
pressure sensing lead 12
first and second lead conductors 14 and 16
proximal connector end 18
pressure sensor capsule or module 20
inner insulating sleeve 22
exterior insulating connector sleeve 24
distal tine assembly 26
crimp pin 27
tip core 28
in-line connector assembly 30
further coiled wire segment 32
further insulating sleeve 34
inner connector pin 36
stylet receiving, pin lumen 38
insulating sleeve 40
connector ring 42
outer sleeve 46
parallel side walls 47, 49
crimp sleeve 48
titanium outer housing half members 50 and 52
flat interior surface 51
diaphragm perimeter 53
diaphragm 54
assembled titanium housing 55
insulating body 56
distal conductive transition sleeve 57
inner conductive transition pin 58
proximal outer conductive transition sleeve 59
ceramic hybrid circuit substrate 60
substrate back side 61
resistor 62
IC chip 64
crimp sleeve 66
inner core sleeve 68
proximal and distal silicone rubber cushions 70 and 72
adaptor ring 74
nose element extension pin 75
feedthrough 76
ceramic insulator 77
nose element 78
feedthrough ferrule 79
feedthrough wire 80
crimp pin 81
polyurethane jacket 82
rectangular inner capacitor plate 84
outer ring-shaped capacitor plate 86
plated standoffs 88, 90, 92,
plated substrate feedthroughs 96 and 98
monitor 100
activity sensor 106
battery 108
crystal 110
input/output circuit 112
microcomputer circuit 114
on-board circuit 116
off-board circuit 118
microprocessor 120
system clock 122
on-board RAM and ROM chips 124 and 126
separate RAM/ROM chip 128
data communications bus 130
digital controller/timer circuit 132
telemetry antenna 134
RF transmitter/receiver 136
crystal oscillator 138
Vref/BIAS circuit 140
ADC/MUX circuit 142
RF transmitter/receiver circuit 142
power-on-reset (POR) circuit 148
pressure and temperature signal demodulator 150
optional activity circuit 152
resistors 151, 152 153
AC current sensor 154
capacitor 155
power supply 156
resistor 157
level shifter 158
resistor 159
flip-flop 160
capacitor 161
digital signal processor 162
pressure signal processing channel 163
temperature signal processing channel 164
filter resistors 166, 169, 171, 173, 186
filter capacitors 165, 167, 175, 182, 184
first pressure signal amplifier 168
second pressure signal amplifier 170
8-bit offset DAC 172
integrator controller 174
bi-directional switch 176
temperature signal amplifier 178
4-bit gain switched resistor networks 180, 181
integrator capacitor 187
integrator resistor 188
sample and hold capacitor 190
biasing resistors 191, 192, 193
integrator 194
temperature amplifier stage 195
Butterworth filter network 196
first pressure amplifier stage 197
second pressure amplifier stage 198
pressure and temperature signal modulating circuit 200
lead leakage resistance 202
lead capacitance 204
series resistances 206 and 208
series resistances 210 and 212
current dividing diode network 214, 216, 218, 220, 222
current amplifier 230
current sources 232, 234, 236
comparators 240, 242
series charge resistors 244, 246
inverters 248, 250
flip-flop 252
semiconductor switches 254, 256, 258, 260, 262, 263, 264
64 I current source 266
144 I current source 268
delay circuit 270
⅔ I current source 272
⅓ I current source 274

We claim:

1. A capacitive pressure and temperature sensing system for providing signals representative of magnitude of body fluid absolute pressure at a selected site and ambient operating conditions, including body temperature at the site comprising:

an elongated implantable lead body having proximal and distal end sections and having first and second electrical conductors extending from the proximal end section to the distal end section, said distal end section adapted to be implanted in a selected body site;

a sensor module formed in the distal end section of the lead body having pickoff and reference capacitor means formed therein and sharing a common charge plate;

sensor circuit means within said sensor module electrically connected to said pickoff and reference capacitor means and said first and second electrical conductors including temperature conversion means for generating a charge current and a discharge current varying with ambient temperature at the selected site, charging and discharging means for alternately charging and discharging said pickoff and reference capacitor means with said charge and discharge currents between selected voltage levels, and pulse generating means for generating pickoff and reference timing pulses separating pressure related and temperature related charge time intervals of said pickoff and reference capacitor means varying as a function of said charge current and capacitance changes of said pickoff capacitor means;

means for providing a bias voltage and current to said first and second electrical conductors for powering said sensor circuit means; and demodulating means coupled to said first and second conductor means and responsive to said pickoff and reference timing pulses for discriminating and converting said pressure and temperature related time intervals into pressure and temperature signals.

2. The sensing system of claim 1 wherein said demodulating means further comprises:

discriminating means for discriminating said pressure and temperature related charge time intervals from said pressure and reference timing pulses;

temperature signal processing channel means for converting temperature related charge time intervals into a temperature signal having a magnitude dependent on temperature induced changes in said charge current affecting charge time of said reference capacitor means; and pressure signal processing channel means for converting the duty cycle of the successive pressure and related charge time intervals into a pressure signal having a magnitude dependent on the pressure induced changes in capacitance of said pickoff capacitor means and also dependent on temperature induced changes in said charge current affecting the charge time of said pickoff capacitor means and said reference capacitor means.

3. The sensing system of claim 2 wherein said temperature signal processing channel means further comprises an integrator for integrating said temperature related charge time interval into an integrated voltage varying in amplitude with the duration of the temperature related charge time interval.

4. The sensing system of claim 3 wherein said pressure signal processing channel means further comprises filter means and amplifier means for low pass filtering and averaging of duty cycles of successive pressure and temperature related charge time intervals to derive said pressure signal.

5. The sensing system of claim 4 wherein said temperature signal processing channel means further comprises:

means for calibrating said integrator to capacitance of said reference capacitor means including adjustable current means for providing an integration current of a magnitude providing an integrated voltage amplitude matching a reference voltage amplitude within a calibration integration time interval.

6. The sensing system of claim 3 wherein said temperature signal processing channel means further comprises:

means for calibrating said integrator to capacitance of said reference capacitor means including adjustable current means for providing an integration current of a magnitude providing an integrated voltage amplitude matching a reference voltage amplitude within a calibration integration time interval.

7. The sensing system of claim 2 further comprising:

means for processing said pressure related charge time intervals into fixed amplitude, square wave voltage signals: and wherein said pressure signal processing channel means further comprises filter means and amplifier means for low pass filtering and averaging of duty cycles of said fixed amplitude voltage signals to derive said pressure signal.

8. The sensing system of claim 2 wherein:

said filter means provides low pass filtering out of signal components reflecting frequency of repetition of said fixed amplitude square wave voltage signals to provide a filtered voltage signal reflecting an average amplitude thereof; and said amplifier means further comprises:

offset adjustment means at an input of said amplifier means for adjusting magnitude of the filtered voltage signal to offset atmospheric pressure and system tolerances; and gain adjustment means for varying gain of said amplifier means to conform the filtered voltage signal with a predetermined voltage range, whereby said pressure signal is derived therefrom.

9. The sensing system of claim 8 further comprising:

means for converting the pressure and temperature signals into digitized data; and means for storing the digitized data for retrieval.

10. The sensing system of claim 1 further comprising:

means for converting the pressure and temperature signals into digitized data; and means for storing the digitized data for retrieval.

11. A capacitive pressure and temperature sensing system for providing signals representative of magnitude of body fluid absolute pressure at a selected site and ambient operating conditions, including body temperature at the site comprising:

an elongated implantable lead body having proximal and distal end sections and having first and second electrical conductors extending from the proximal end section to the distal end section, said distal end section adapted to be implanted in a selected body site;

a sensor module formed in the distal end section of the lead body having pickoff and reference capacitor means formed therein and sharing a common charge plate;

sensor circuit means within said sensor module electrically connected to said pickoff and reference capacitor means and said first and second electrical conductors including temperature conversion means for generating a charge current and a discharge current varying with ambient temperature at the selected site, charging and discharging means for alternately charging and discharging said pickoff and reference capacitor means with said charge and discharge currents between selected voltage levels, and pulse generating means for generating pickoff and reference timing pulses separating pressure related and temperature related charge time intervals of said pickoff and reference capacitor means varying as a function of said charge current and capacitance changes of said pickoff capacitor means;

means for providing a bias voltage and current to said first and second electrical conductors for powering said sensor circuit means; and demodulating means coupled to said first and second conductor means and responsive to said pickoff and reference timing pulses for discriminating and converting said pressure and temperature related time intervals into pressure and temperature signals wherein said sensor module further comprises:
pressure deformable pickoff capacitor means having a nominal capacitance at atmospheric pressure for varying in pickoff capacitance in response to variations in fluid pressure at the selected body site having a first plate coupled to said first electrical conductor and a second spaced apart plate; and reference capacitor means having a nominal capacitance as the pickoff capacitor means at atmospheric pressure and not substantially varying in capacitance substantially the in response to variations in fluid pressure at the selected body site and having a first plate coupled to said first electrical conductor and a second spaced apart plate.

12. The sensing system of claim 11 wherein said sensor circuit means further comprises:

means responsive to said bias voltage for defining a target voltage level, a discharge voltage level and a reference voltage level between said target and discharge voltage levels; and wherein said charging and discharging means further comprise:

means for alternately charging said pickoff and reference capacitor means with said charge current from said discharge voltage level to said target voltage level; and means operable upon charging of each of said pickoff and reference capacitor means to said target voltage level for discharging said pickoff and reference capacitor means from said target voltage level to said discharge voltage level with said discharge current.

13. The sensing system of claim 12 wherein said pulse generator means further comprises:

means responsive to charging of said reference capacitor means to said target voltage and discharging of said reference capacitor means from said target voltage level to said reference voltage level for generating a pressure timing pulse on one of said first and second conductors having a first distinguishable parameter; and means responsive to the charging of said pickoff capacitor means to said target voltage and discharging of said pickoff capacitor means from said target voltage level to said reference voltage level for generating a reference timing pulse on one of said first and second conductors having a second distinguishable parameter differing from said first distinguishable parameter capable of being discriminated by said demodulating means.

14. The sensing system of claim 13 wherein said first and second distinguishable parameters comprise amplitudes and pulse widths of reference timing signals and pressure timing signals.

15. The sensing system of claim 14 wherein said demodulating means further comprises:

means responsive to said first and second distinguishable parameters for detecting and discriminating said pressure timing signals from said reference timing signals;

temperature signal processing channel means responsive to a detected pressure timing signal for converting a following temperature related charge time interval ending on occurrence of succeeding temperature timing signal into a temperature signal having a magnitude dependent on temperature induced changes in said charge current affecting the charge time of said reference capacitor means; and pressure signal processing channel means responsive to a detected temperature timing signal for converting a following pressure related charge time interval ending on occurrence of a succeeding pressure timing signal into a pressure signal having a magnitude dependent on the pressure induced changes in capacitance of said pickoff capacitor means and also dependent on temperature induced changes in said charge current affecting charge time of said pickoff capacitor means and said reference capacitor means.

16. The sensing system of claim 15 wherein said temperature signal processing channel means further comprises an integrator for integrating said temperature related charge time interval into an integrated voltage varying in amplitude with the duration of the temperature related charge time interval.

17. The sensing system of claim 16 wherein said pressure signal processing channel means further comprises filter means and amplifier means for low pass filtering and averaging of duty cycles of successive pressure and temperature related time intervals to derive said pressure signal.

18. The sensing system of claim 15 wherein said pressure signal processing channel means further comprises filter means and amplifier means for low pass filtering and averaging of duty cycles of successive pressure and temperature related time intervals to derive said pressure signal.

* * * * *

UNITED STATES PATENT AND TRADEMARK OFFICE
CERTIFICATE OF CORRECTION

PATENT NO. : 5,535,752

DATED : JULY 16, 1996

INVENTOR(S) : HALPERIN ET AL.

It is certified that error appears in the above-identified patent and that said Letters Patent is hereby corrected as shown below:

Col. 12, line 27: "be detected" should read --can be detected--

Col. 30, line 31: "convening" should read --converting--

Col. 29, line 32: delete "substantially the"

Signed and Sealed this

Twenty-ninth Day of May, 2001

Attest:

NICHOLAS P. GODICI

*Attesting Officer*  *Acting Director of the United States Patent and Trademark Office*